United States Patent [19]

Flom et al.

[11] 4,053,953
[45] Oct. 18, 1977

[54] POSTERIOR CHAMBER ARTIFICIAL INTRAOCULAR LENS WITH RETAINING MEANS AND INSTRUMENTS FOR USE THEREWITH ADAPTED TO PROVIDE EXTRAOCULAR CONFIRMATION OF OPERATIVE ENGAGEMENT

[76] Inventors: Leonard Flom, Arlen Road, Westport, Conn. 06880; Kenneth J. Rodgerson, 83 Melville Ave., Fairfield, Conn. 06430

[21] Appl. No.: 731,139

[22] Filed: Oct. 12, 1976

Related U.S. Application Data

[63] Continuation-in-part of Ser. No. 648,936, Jan. 14, 1976, Pat. No. 3,991,426, which is a continuation-in-part of Ser. No. 549,853, Feb. 14, 1975, abandoned.

[51] Int. Cl.² .......................... A61F 1/16; A61F 1/24; A61F 9/00
[52] U.S. Cl. ...................................... 3/13; 128/303 R
[58] Field of Search ...................... 3/13, 1; 128/303 R; 351/160

[56] References Cited

U.S. PATENT DOCUMENTS

| 2,952,023 | 9/1960 | Rosen | 3/13 |
| 3,074,407 | 1/1963 | Moon et al. | 128/303 R |
| 3,454,966 | 7/1969 | Rosen | 3/13 |
| 3,866,249 | 2/1975 | Flom | 3/13 |
| 3,913,148 | 10/1975 | Potthast | 3/13 |

Primary Examiner—Ronald L. Frinks
Attorney, Agent, or Firm—Wooster, Davis & Cifelli

[57] ABSTRACT

Artificial intraocular lenses comprise an optical zone portion for implanting in the posterior chamber of an eye, posts extending from said optical zone portion through the iris into the anterior chamber thereof, and retaining means for securing to the ends of the posts, whereby said posts and retaining means hold and position the artificial intraocular lenses within the eye. In some embodiments, the posts and retaining means are configured for an interengaging press fit. In another embodiment the posts are attached to the retaining means and are adapted to be secured to the optical zone portion. Instruments aiding in the implanting of the artificial intraocular lenses in the eye by press fitting the retaining means to the posts, comprise means for supporting the retaining means on the instrument, bridle means connecting the optical zone portion of the artificial intraocular lenses with the instrument, and means for drawing the posts toward the retaining means until the desired interengaging press fit therebetween is achieved. The instruments are also adapted to attach the posts of the retaining means to the lens portion in the other embodiment. The instruments are also modified to remove the retaining ring from the posts. The artificial intraocular lenses and instruments are adapted to provide an extra-ocular confirmation signal indicating that the posts are operatively engaged for holding the optical zone portion and retaining means together. Conductive portions of the optical zone portion and retaining means contact to close an electrical circuit providing the extra-ocular confirmation signal.

18 Claims, 45 Drawing Figures

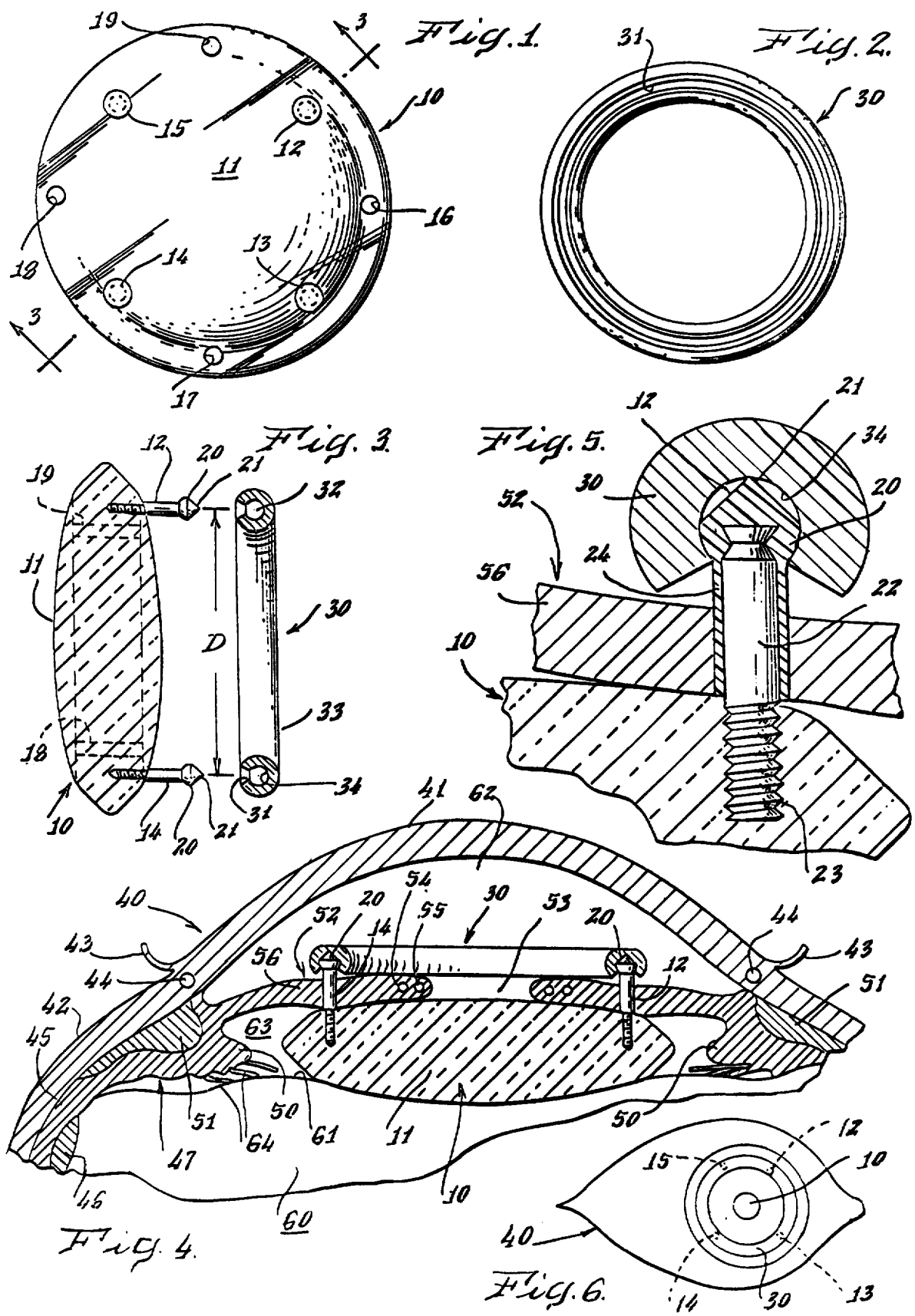

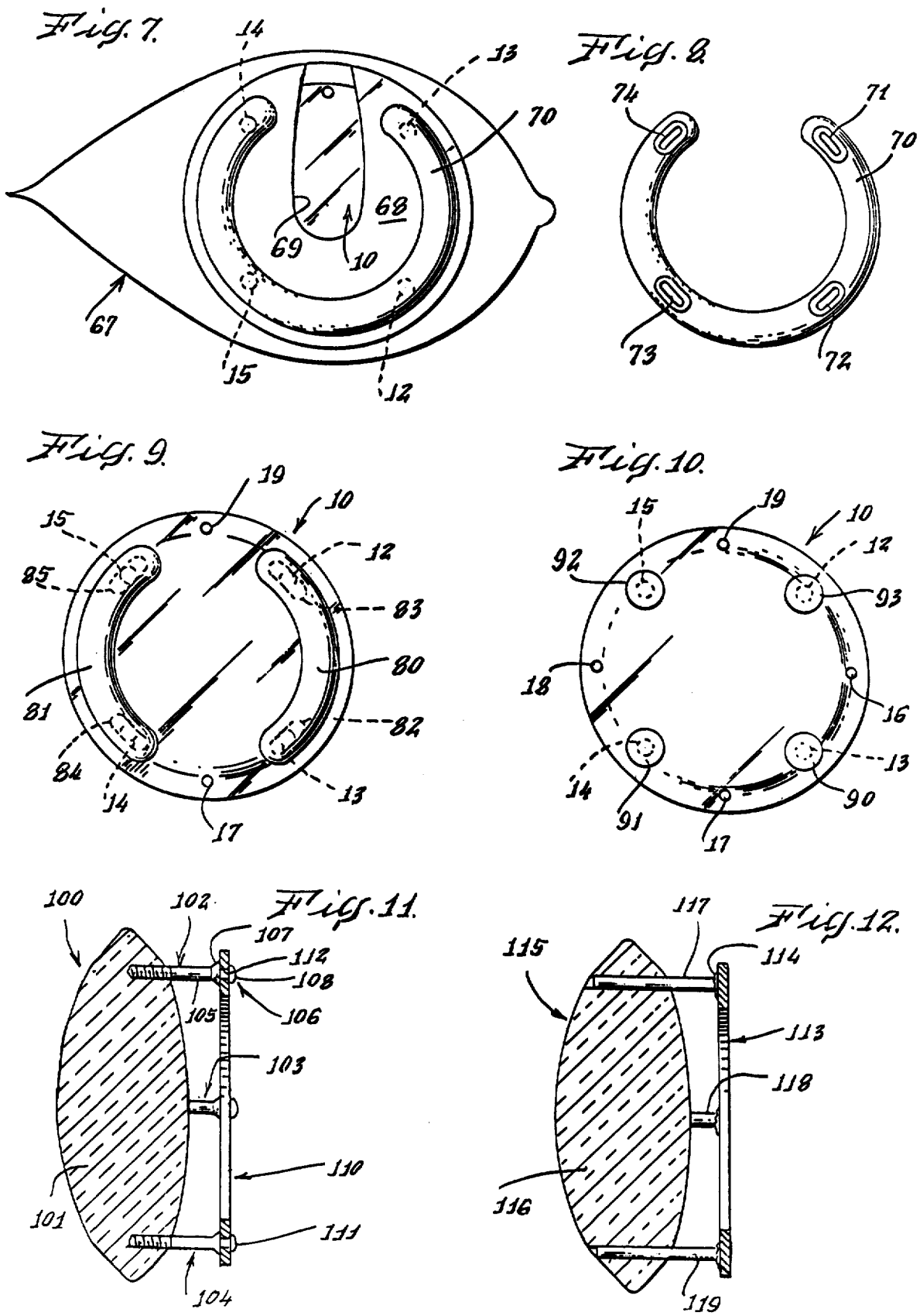

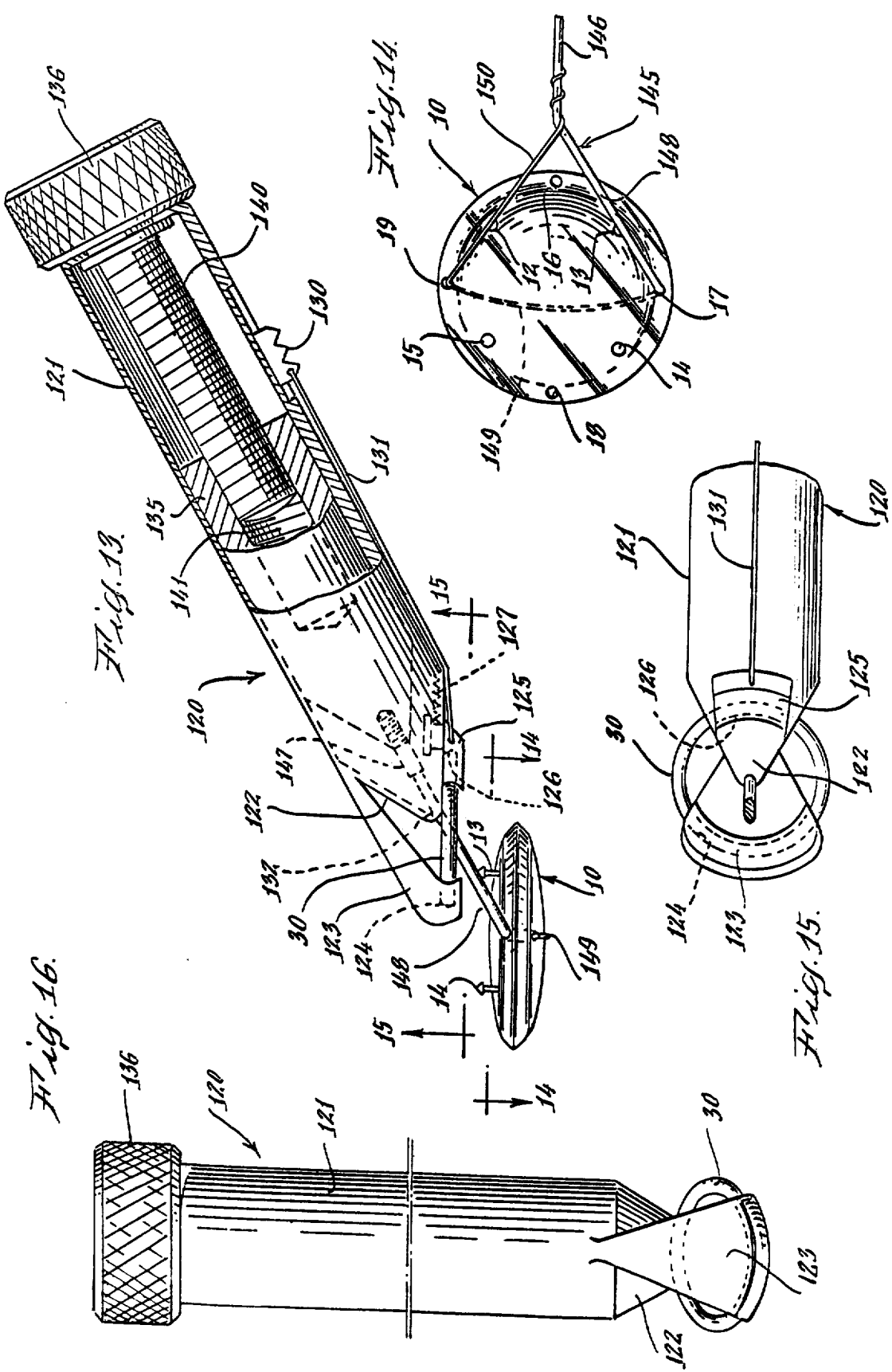

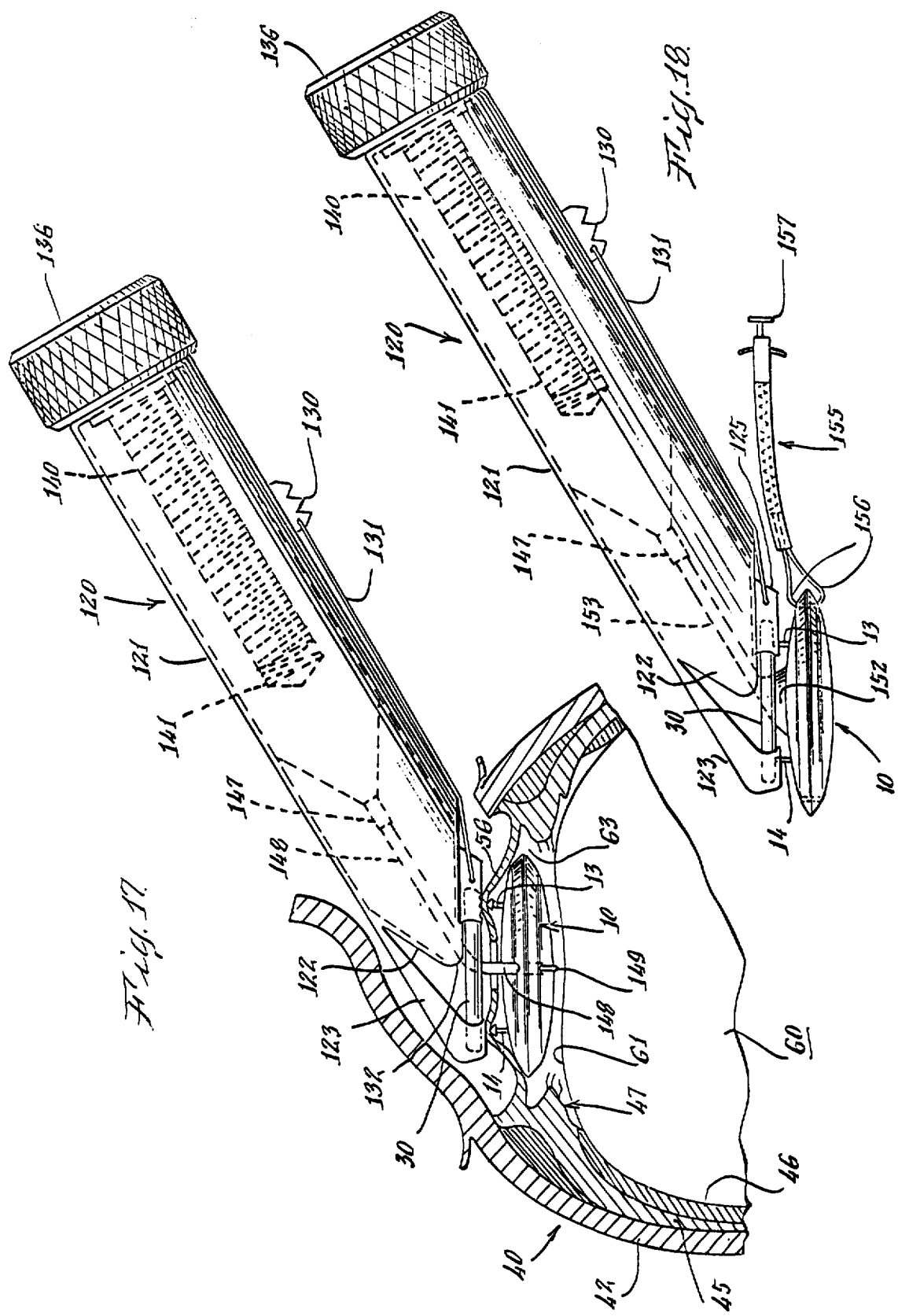

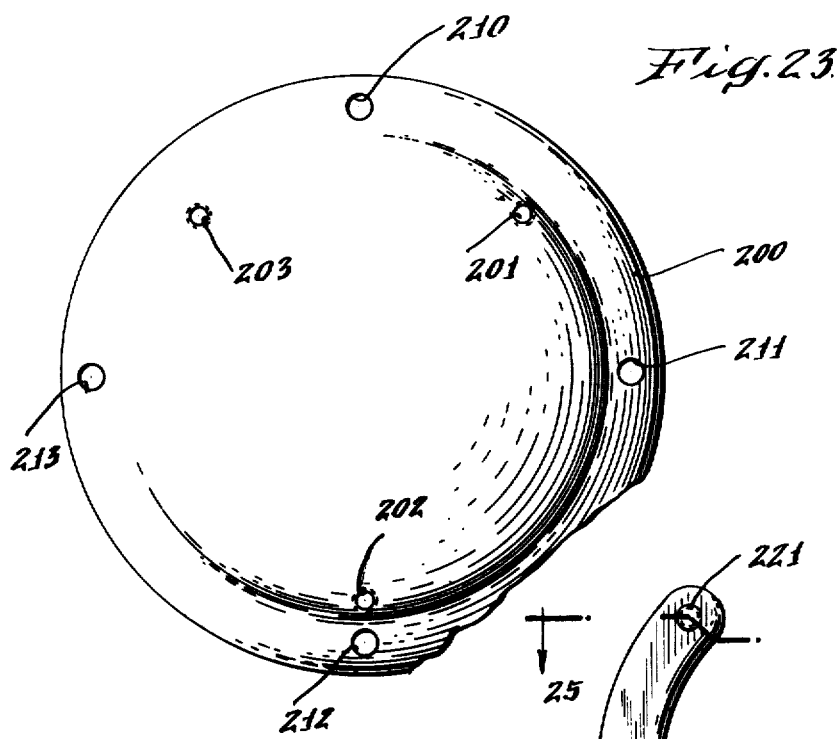
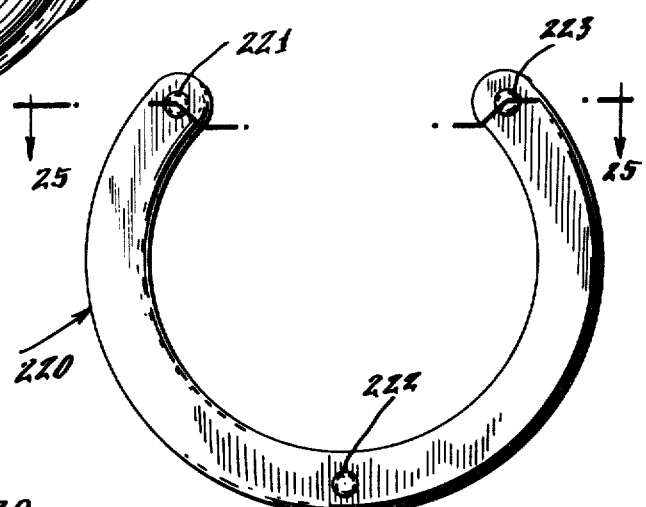
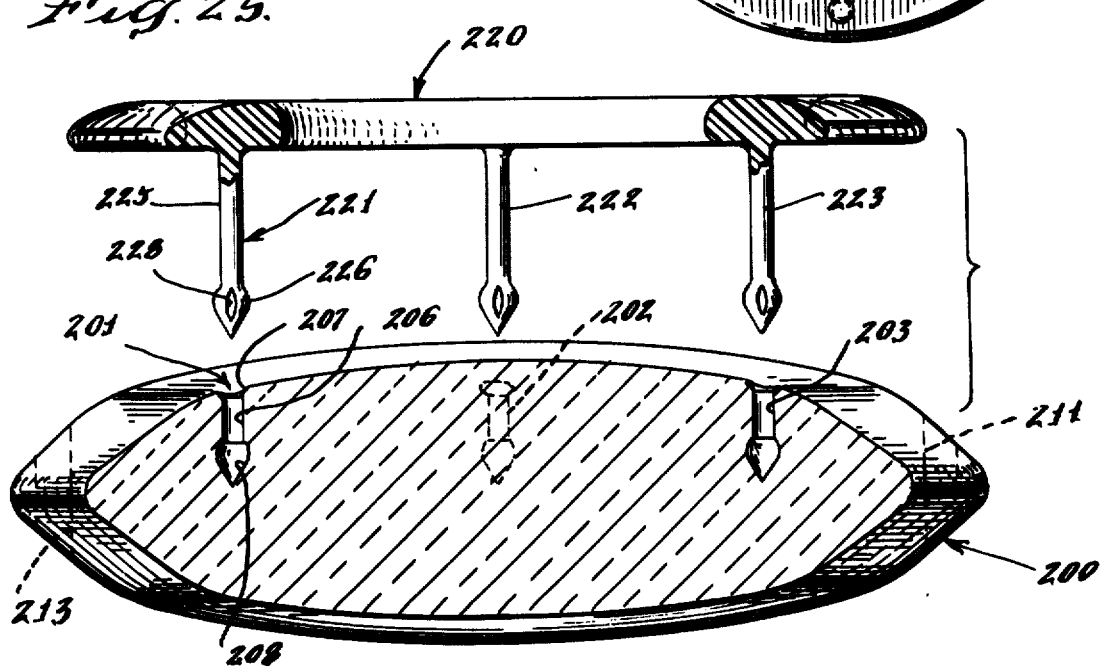

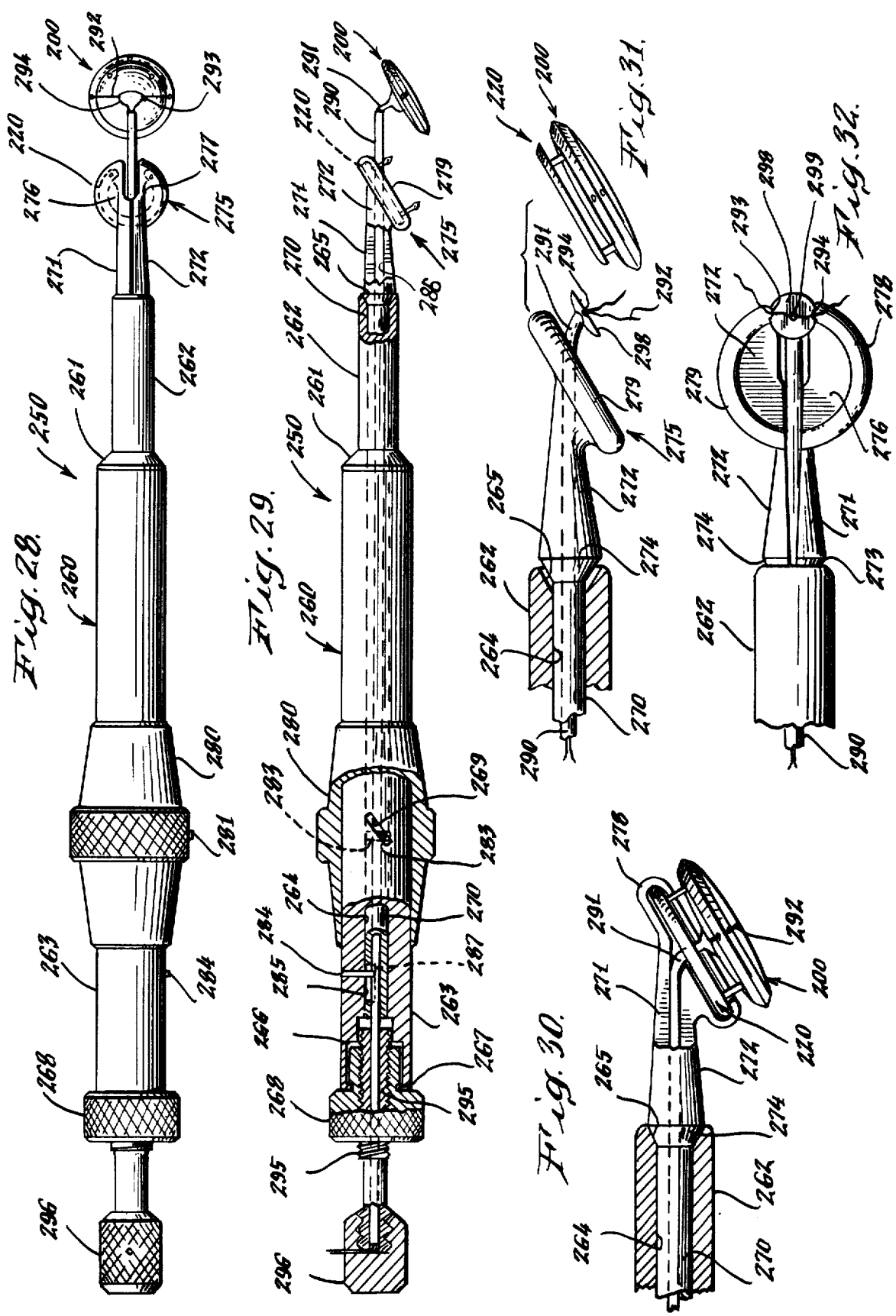

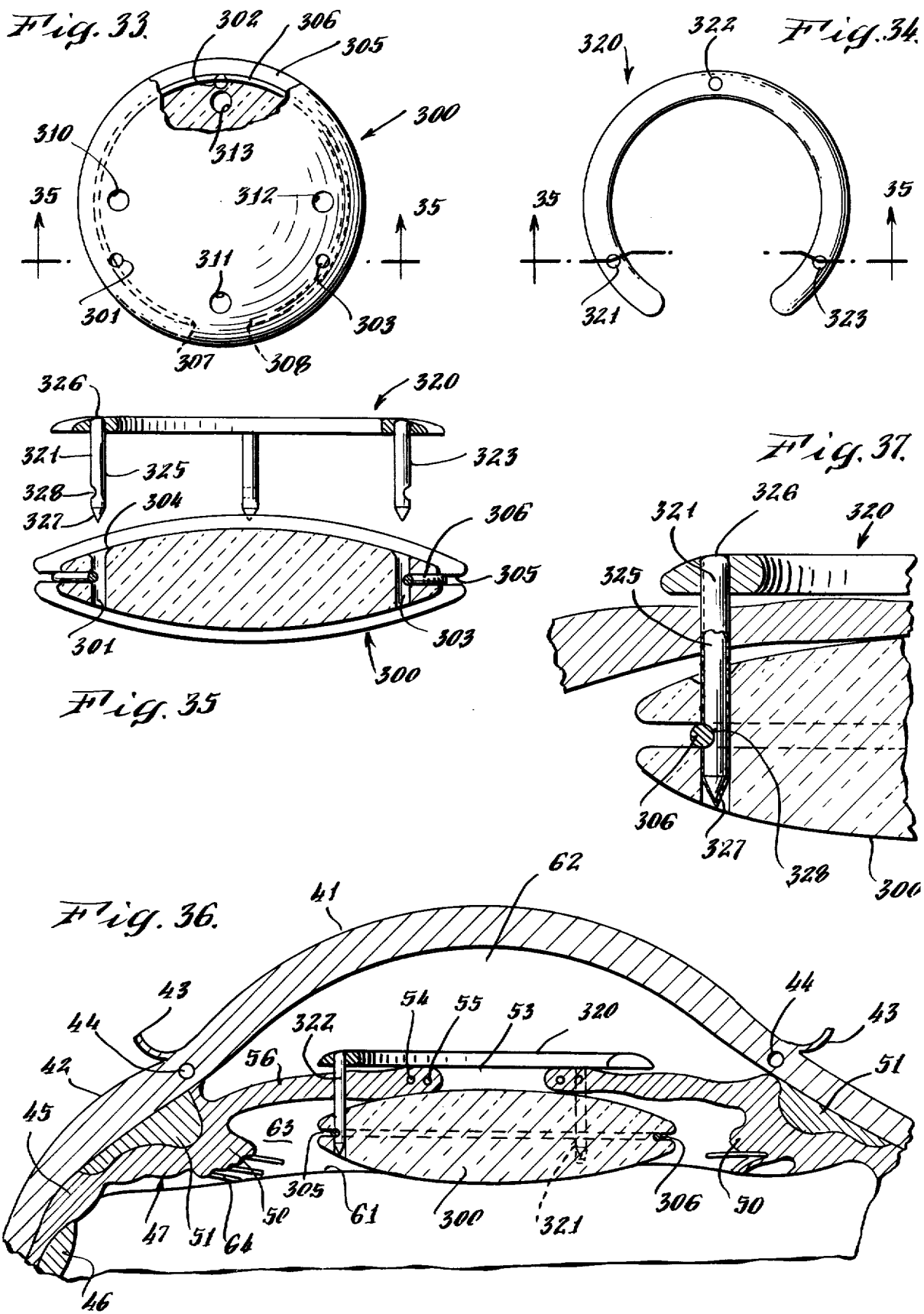

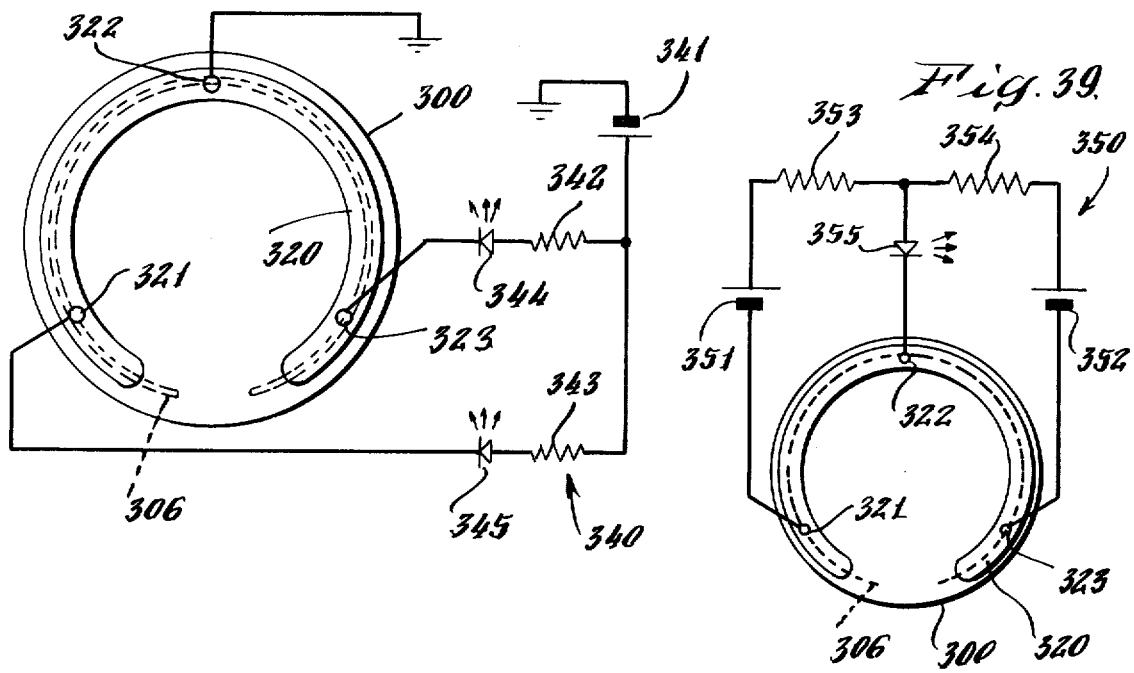
Fig. 38.
Fig. 39.
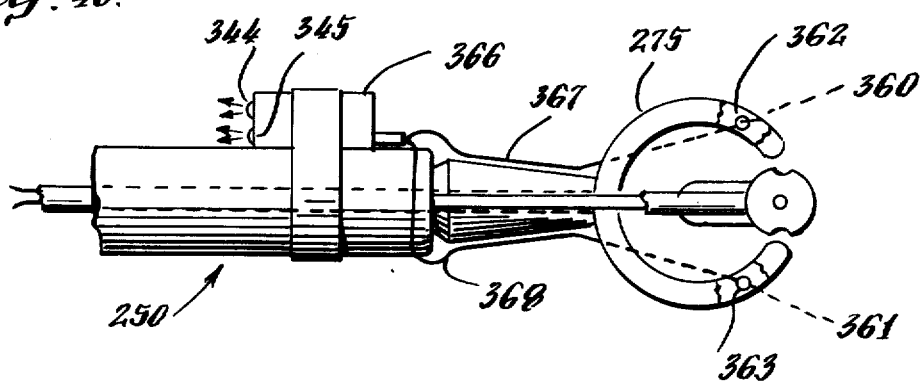
Fig. 40.
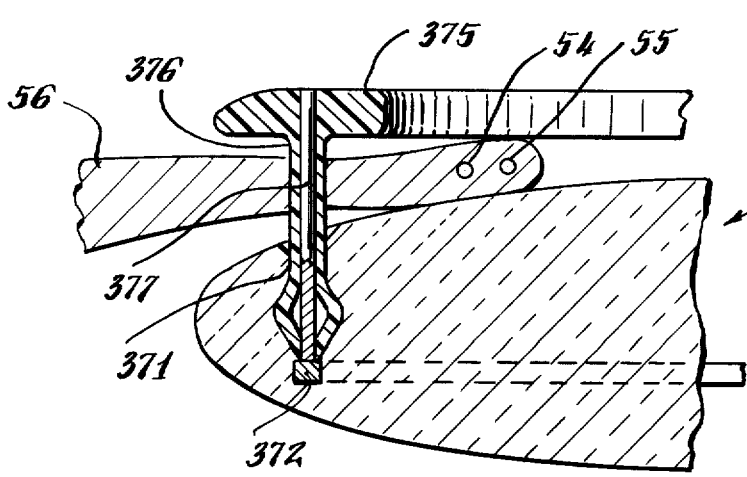
Fig. 41.

POSTERIOR CHAMBER ARTIFICIAL INTRAOCULAR LENS WITH RETAINING MEANS AND INSTRUMENTS FOR USE THEREWITH ADAPTED TO PROVIDE EXTRAOCULAR CONFIRMATION OF OPERATIVE ENGAGEMENT

This application is a continuation-in-part of our application, Ser. No. 648,936, filed Jan. 14, 1976, now U.S. Pat. No. 3,991,426, which application was a continuation-in-part of our application, Ser. No. 549,853, filed Feb. 14, 1975, now abandoned.

BACKGROUND

1. Field of the Invention

This invention relates to an artificial intraocular lens for implantation in the posterior chamber of the eye to obviate aphakia, the lens including retaining means, and further relates to instruments for implanting and removing the artificial intraocular lens, including respectively attaching and detaching the retaining means, wherein the lens, retaining means and instruments cooperate to provide confirmation that the lens and retaining means have been operatively engaged during implantation.

2. Prior Art

When no lens is present in the eye, which is known as the aphakic condition or aphakia and is usually the result of intracapsular or extracapsular lens extraction, the eye does not have the ability to focus rays of light. Therefore, the eye receives a blurred image and vision is impaired.

The most common solution for providing a focusing mechanism to obviate the aphakic condition is to interpose contact lenses or spectacles or a combination thereof between the eye and the light entering therein. However, both contact lenses and spectacles have drawbacks when used in the treatment of aphakia. Neither spectacles nor contact lenses can duplicate the natural optical system because they are positioned outside of the eye, which results in a shift of the optical center from the in vivo state. Because the optical center has been shifted, the image received by the eye is either distorted and/or changed in size. In particular, spectacles and/or contact lenses usually cannot be used to restore exactly binocular vision after removal or loss of the lens from one eye when the other eye continues to function normally.

Further, the most common reason for removal of a lens is the condition of lenticular opacity known as a cataract, which occurs primarily in aged persons who have difficulty in adjusting to contact lenses and in manipulating the contact lenses for insertion and removal. Cataracts are also common in animals, such as dogs and horses, and contact lenses and/or spectacles are not suitable devices for their treatment.

The desirability of implanting an artificial lens within the eye to obviate the conditon of aphakia is well-known and accepted in countries such as England, Holland and Italy. However, practical devices for carrying out this desirable objective have not been perfected, although several devices have been used with a modicum of success.

In approximately 1950 Harold Ridley developed an artificial intraocular lens which comprised an optical lens portion having three foot-like projections or "feet" extending radially outward therefrom. Ridley originally placed this lens in the posterior chamber of the eye, behind the iris, with the feet resting against the ciliary body between the ciliary process and the base of the iris. However, positioning of this lens in the posterior chamber was abandoned because of instances of dislocation after implantation and failures from glaucoma and the like, probably caused by irritation of the ciliary body by the feet.

Ridley's failure with posterior chamber artificial lenses led him and others, such as D. P. Choyce, to turn their attention to intraocular artificial lenses implanted in the anterior chamber of the eye between the iris and the cornea. The particular lens used was similar to Ridley's original lens, and had radially protruding feet which accomplished positioning of the lens in front of the pupil. These efforts also met with limited success, primarily because of the problems of irritation of the eye by the supporting feet and dislocation of the lens from its desired position in front of the pupil.

It should be noted that placement of the lens in the anterior chamber is an unnatural position, with the attendant problems of restoring accurate binocular vision. Also, an anterior chamber lens is not positioned adjacent to the hyaloid membrane for supporting the vitreous humor, and instances of forward displacement of the vitreous humor and retinal detachment are more likely to occur when anterior chamber lenses are used.

E. Epstein and C. D. Binkhorst developed artificial intraocular lenses which rely on the constrictor muscle of the iris as the positioning mechanism. Epstein first designed a "collar-stud" implant, with the pupil constricted in its waist for positioning thereof. Copeland's "Maltese Cross" pupil-supported implant has two leaves anterior to the iris and two leaves at right angles to the others and behind the iris. Binkhorst developed an iridocapsular (two-loop) lens and an iris-clip (four-loop) lens. The former comprises a lens of larger diameter than the pupil and placed thereover so that the periphery engages the front of the iris, and further comprises two metal loops which protrude from the back of the lens and extend generally parallel with the back surface of the lens and behind the iris for clipping the lens to the iris. Binkhorst's iris-clip lens is similar except that the iris is held by two pairs of loops which flank the iris and support the lens in front of the pupil. In some instances, the iris is sutured to the clips to secure the positioning of the lens. This type of lens is also unsatisfactory in several respects. It, by necessity, interferes with constriction of the pupil, and in fact fixes the size of the pupil. It is also an anterior chamber lens, wherein correct positioning of the optical center cannot be achieved.

J. G. F. Worst considered posterior placement of an artificial lens to be desirable, but developed a lens having a pair of closely spaced openings for positioning in front of the iris. A suture was placed through the two openings and attached the lens to the iris. Although it is not believed that Worst's suture would cause irritation of the ciliary body, as did the earlier posterior lens of Ridley, the difficulty of the technique necessary to suture the lens in position without damaging the iris as well as the possibility that the suture would not hold or would tear out from the iris has limited the acceptance of Worst's lens.

Additional artificial lenses designed for positioning in the posterior chamber are described in U.S. Pat. No. 3,711,870 to Deitrick and in U.S. Pat. No. 3,673,616 to Fedorov et al. Deitrick's lens comprises a central optical portion surrounded by a resilient silicone flange shaped to receive and nest against the ciliary body. The lens is to be held in place by suturing the resilient flange to the ciliary body. Although the medical worth of the Deitrick lens is not yet known, it is known that it would be difficult to place sutures where Deitrick directs and it is also known that there may be reluctance on the part of ophthalmologists or ophthalmologic surgeons to do so because of the many risks attendant with the irritation of the ciliary body. Fedorov et al's lens is supported in the eye by radially protruding prongs flanking the iris and gripped by the constrictor muscles of the iris adjacent to the pupil, in somewhat the same manner as the Binkhorst lens.

Several of the prior art lenses are discussed in an article by D. P. Choyce entitled "History of Intraocular Implants" which is printed in Annals of Ophthalmology, October, 1973. The article also includes a list of references from which further information concerning prior art intraocular lenses can be obtained.

Several of the above lenses rely on sutures placed in the iris for holding the lenses in position. It should be noted that the iris consists of spongy, flexible tissue which may be pulled and stretched to a limited degree without damaging it. However, the iris has the unique property of never healing together after being cut or damaged. Thus, if a suture pulls through the iris, the damage to the iris is permanent. Because sutures are generally of a small diameter, if a lens positioned and held by sutures is subjected to a dislocating force, the sutures may cut the iris, resulting in permanent damage.

SUMMARY OF THE INVENTION

The artificial intraocular lens according to the invention herein is adapted for implantation in the posterior chamber, wherein all the advantages of natural positioning of the lens are achieved. The artificial intraocular lens is held in place by a plurality of posts extending forwardly from the lens and protruding through the iris into the anterior chamber. Retaining means are secured to the posts in the anterior chamber of the eye adjacent to the iris. In a first embodiment, the retaining means preferably comprises a retaining ring which is press fit onto the ends of the posts in the anterior chamber, although the retaining means may comprise a partial ring or even individual retaining members for each post.

In another embodiment, the posts are integral with the retaining means, which may be a whole or partial ring, and the posts are inserted through the iris and press-snap fit into openings in the lens. This embodiment is preferable because of the ease with which its optical lens portion can be inserted behind the iris, but the engagement of the posts in the lens openings cannot be observed. Therefore, in this embodiment the lens preferably includes a conductor such as wire connecting the openings, and the posts of the retaining means are also conductive, such that when the posts are operatively engaged in the openings, conductive contact is achieved between the posts and the wire. Portions of the posts positioned in the anterior chamber are connected temporarily into an electrical circuit which is completed to provide a signal as extra-ocular confirmation when all of the posts are in fact operatively engaged in their respective lens openings.

Although it is possible to visually ascertain the engagement of the posts and retaining means in the first embodiment, it is preferable to include means for providing extra-ocular confirmation of the engagement. To this end, the posts may be conductive and be connected by a conductor positioned in the lens portion, and the retaining means includes metal portions which are contacted by the posts upon proper engagement. The metal portions of the retaining means also function as contacts for temporarily establishing a circuit which is completed if the requisite post-retaining means contact is extant. Alternatively, the retaining means may provide a conductive path or paths connecting conductive posts, and the posts may be used as contacts to a circuit providing an extra-ocular confirmatory signal.

In both embodiments, the iris is held loosely constrained between the artificial intraocular lens and the retaining means with the posts extending through the iris, whereby the artificial intraocular lens is held in the desired position. The retaining means are arrayed about and separated from the pupil and do not interfere with vision. Openings through the artificial intraocular lens are provided near the periphery to permit the free flow of aqueous, which is produced by the ciliary body, and to aid in the manipulation and implantation of the artificial intraocular lens.

Thus, the artificial intraocular lens according to the invention herein is firmly held in a natural position, which is the posterior chamber of the eye. The artificial intraocular lens according to the invention herein avoids any contact with the ciliary body, presents a smooth surface to the endothelium of the cornea as well as to the hyloid membrane, does not interfere with the constrictor and dilator muscles of the iris adjacent to the pupil, and does not contact the area of Schlemm's canal. Thus, these and any other sensitive anatomical areas of the eye are not irritated by the artificial intraocular lens according to the invention herein. True binocular vision may be achieved with the posterior chamber artificial intraocular lens according to the invention herein, and forward displacement of the vitreous humor and consequent cystoid macular endema and/or retinal detachment are avoided.

Instruments are also provided for implanting the artificial intraocular lenses. These instruments make the techniques for implantation within the range of capability of the average ophthalmological surgeon.

A first embodiment of an instrument according to the invention herein and well adapted for use with the first embodiment of the artificial intraocular lenses generally comprises a handle configured to hold the retaining ring, or other retaining means adapted to press fit onto the posts of the artificial intraocular lens. A bridle attaches the artificial intraocular lens to a member slidably mounted in the instrument with respect to the retaining ring. The bridle is sufficiently rigid to aid in inserting the artificial intraocular lens through the dilated pupil and into the posterior chamber. A thumbwheel or other controlled adjusting mechanism is provided to drive the slidably mounted member and to thereby cause relative movement of the retaining ring into position over the posts of the artificial intraocular lens, and finally to press fit the retaining ring onto the posts. Means are provided to release the retaining ring from the instrument and the bridle can be easily severed, whereafter the instrument can be removed, leaving the artificial intraocular lens and attached retaining means implanted within the eye.

The instrument may also be provided with a rigid forwardly protruding foot attached to the slidably mounted member, wherein by reversing the rotation of the thumbwheel or other drive means, the retaining ring can be lifted from the posts to release the artificial intraocular lens for removal. A lens snare may also be provided to aid in extracting the lens.

A second embodiment of an instrument according to the invention herein is particularly well adapted for implanting the artificial intraocular lens in which the posts are integral with the retaining ring and press-snap fit into the lens. The second embodiment instrument also comprises a handle configured to releasably hold the retaining ring. A thin member is slidably mounted in the handle, extends therefrom through the held ring, and terminates in a foot against which the lens is tightly secured by a thin bridle. Thumbwheel or other adjusting means are provided to drive the slidably mounted rod, causing relative movement of the retaining ring toward the lens until the posts engage the openings in the lens which receive them, and thereafter press-snap joining the retaining ring and the lens. The foot of the thin member, against which the lens is tightly held, accurately positions the lens with respect to the posts of the retaining ring, which is an important feature inasmuch as the lens is blocked from view behind the iris when the lens and ring are joined. The foot also serves to separate the retaining ring from the lens, should removal be necessitated.

The instruments also preferably include conductive contacts for temporarily connecting a circuit having its path through the post-retaining ring contacts, so that an extra-ocular confirmation signal of operative engagement will be provided.

OBJECTS OF THE INVENTION

It is a principal object of the invention to provide an artificial intraocular lens for obviating aphakia.

It is another object of the invention to provide an artificial intraocular lens for implantation into the posterior chamber of the eye.

It is a further object of the invention to provide an artificial intraocular lens which includes means for positioning and holding it within the eye without irritating sensitive portions of the eye.

It is a further object of the invention to provide an artificial intraocular lens and instruments for implanting the same which permit an implantation technique within the range of skills of the average ophthalmological surgeon, and provide extra-ocular confirmation of successful implantation.

Other and more particular objects of the invention will be in part obvious and will in part appear from a perusal of the following description of the preferred embodiments and the claims, taken together with the drawings.

DRAWINGS

FIG. 1 is a front elevation view of an artificial intraocular lens according to the invention herein;

FIG. 2 is a rear elevation view of a retaining ring according to the invention herein for the artificial intraocular lens of FIG. 1;

FIG. 3 is a sectional view of the artificial intraocular lens of FIG. 1 and the retaining ring of FIG. 2;

FIG. 4 is a sectional view of an eye showing the artificial intraocular lens and retaining ring of FIG. 3 implanted therein;

FIG. 5 is a fragmentary enlarged sectional view of a portion of the eye of FIG. 4 having the artificial intraocular lens and retaining ring inplanted therein;

FIG. 6 is a front elevation view of the eye of FIG. 4 having the artifical intraocular lens and retaining ring implanted therein;

FIG. 7 is a front elevation view of another eye having the artificial intraocular lens and a partial retaining ring according to the invention herein implanted therein;

FIG. 8 is a rear elevation view of the partial retaining ring of FIG. 7;

FIG. 9 is a front elevation view of the artificial intraocular lens and dual retaining members according to the invention herein;

FIG. 10 is a front elevation view of the artificial intraocular lens and plural retaining buttons according to the invention herein;

FIG. 11 is a sectional view of another embodiment of an artificial intraocular lens and a retaining ring therefor according to the invention herein;

FIG. 12 is a sectional view of another embodiment of an artificial intraocular lens and a retaining ring therefor according to the invention herein;

FIG. 13 is a side elevation view, partially in section, of an artificial intraocular lens, a retaining ring therefor, and an instrument for implanting the same within an eye, all according to the invention herein;

FIG. 14 is a sectional view taken along the lines 14—14 of FIG. 13 showing a top plan view of the artificial intraocular lens held by a bridle;

FIG. 15 is a sectional view taken along the lines 15—15 of FIG. 13 showing a bottom plan view of the instrument and the retaining ring held thereby;

FIG. 16 is a front elevation view of the instrument of FIG. 13 and the retaining ring held thereby;

FIG. 17 is a side elevation view, partially in section, of the artificial intraocular lens and the retaining ring being implanted into an eye with the instrument of FIG. 13;

FIG. 18 is a side elevation view of an artificial intraocular lens having a retaining ring attached thereto, and the instrument of FIG. 13, said instrument modified for removing the retaining ring from the artificial intraocular lens, all according to the invention herein;

FIG. 23 is a front elevation view of another embodiment of an artificial intraocular lens according to the invention herein;

FIG. 24 is a rear elevation view of a retaining ring according to the invention herein for the artificial intraocular lens of FIG. 23;

FIG. 25 is a side sectional view of the artificial intraocular lens of FIG. 23 and the retaining ring of FIG. 24;

FIG. 28 is a top plan view of an artificial intraocular lens, a retaining ring therefor, and an instrument for implanting the same within an eye, all according to the invention herein;

FIG. 29 is a side elevation view, partially in section, of the artificial intraocular lens, retaining ring and instrument of FIG. 28;

FIG. 30 is a fragmentary view, partially in section, of the artificial intraocular lens, retaining ring and instrument of FIG. 28 showing the lens and retaining ring joined;

FIG. 31 is a fragmentary view, partially in section, of the artificial intraocular lens, retaining ring and instrument of FIG. 28 showing the lens and retaining ring released from the instrument;

FIG. 32 is a bottom view of the instrument of FIG. 28 corresponding to FIG. 31;

FIG. 33 is a front elevation view of another embodiment of an artificial intraocular lens according to the invention herein;

FIG. 34 is a front elevation of a retaining ring according to the invention herein for the artificial intraocular lens of FIG. 33;

FIG. 35 is a sectional view of the artificial intraocular lens of FIG. 33 and the retaining ring of FIG. 34, taken along the lines 35—35 of those Figures;

FIG. 36 is a sectional view of an eye showing the artificial intraocular lens and retaining ring of FIG. 35 implanted therein;

FIG. 37 is a fragmentary enlarged sectional view of a portion of the eye of FIG. 36 having the artificial intraocular lens and retaining ring implanted therein;

FIG. 38 is a front elevation view of the artificial intraocular lens and retaining ring of FIGS. 33 and 34 assembled, and showing an electrical circuit for providing an extra-ocular confirmation signal of engagement between the lens and retaining ring;

FIG. 39 is similar to FIG. 38 and shows an alternate electrical circuit;

FIG. 40 is a bottom view of the instrument of FIG. 28 modified to provide an electrical circuit, signal means, and contact points for connecting the electrical circuit to the artificial intraocular lens and retaining means of FIGS. 33 and 34;

FIG. 41 is a sectional view, partially cut away, of another artificial intraocular lens and a retaining ring according to the invention herein;

Figure 42:
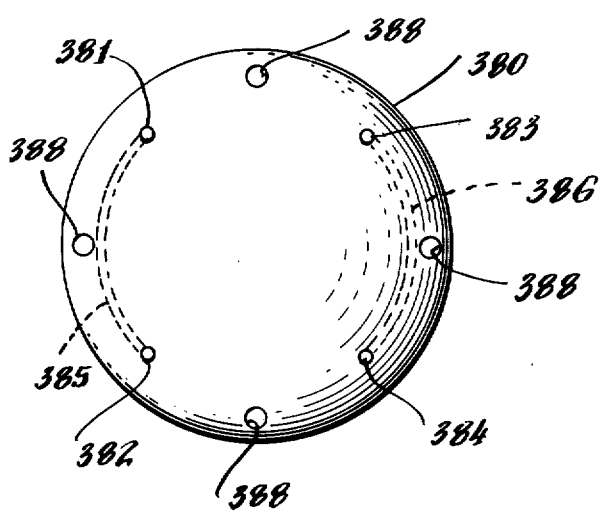
FIG. 42 is a front elevation view of another embodiment of an artificial intraocular lens according to the invention herein.
Figure 43:
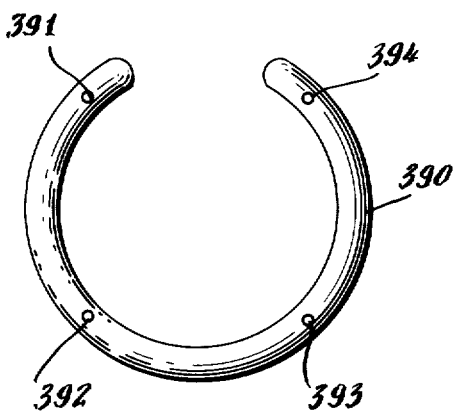
FIG. 43 is a front elevation view of a retaining ring according to the invention herein for the artificial intraocular lens of FIG. 42.
Figure 44:
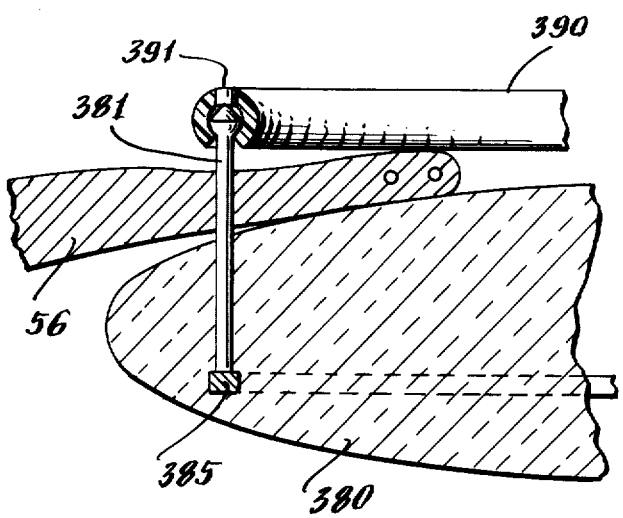
Figure 45:
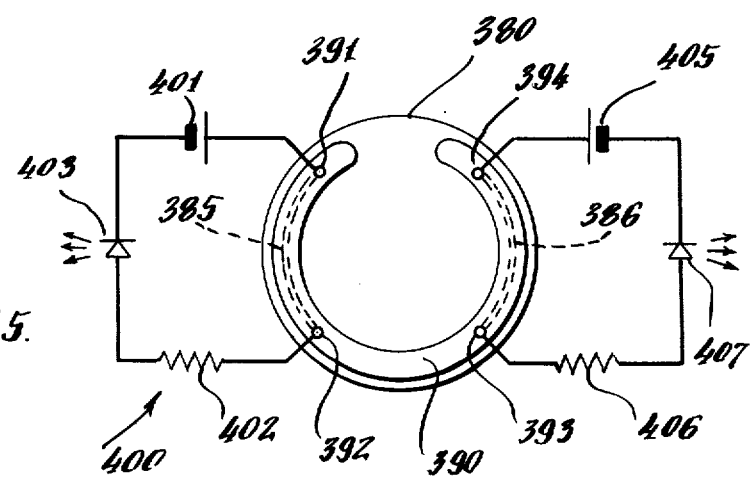

FIG. 44 is a fragmentary enlarged sectional view of the artificial intraocular lens of FIG. 42 and the retaining ring of FIG. 43 assembled together; and FIG. 45 is a front elevation view of the artificial intraocular lens and retaining ring of FIGS. 43 and 44 assembled, and showing an electrical circuit for providing an extra-ocular confirmation signal of engagement between the lens and retaining ring.

The same reference numbers refer to the same elements throughout the various Figures.

PREFERRED EMBODIMENTS

The invention herein relates to an artificial intraocular lens including retaining means for securing the artificial intraocular lens in an eye, several embodiments of which will be described, and to instruments aiding in implanting the artificial intraocular lenses in eyes, and in particular in attaching the retaining means to the implanted artificial intraocular lens, several embodiments of which also will be described. The invention also relates particularly to an artificial intraocular lens including retaining means which complete an electrical circuit when operatively engaged together, wherein the electrical circuit provides an extra-ocular confirmation signal that operative engagement has been achieved.

Referring now to FIGS. 1 — 3, there is shown an artificial intraocular lens 10 and a retaining ring 30 for use with the artificial intraocular lens 10, according to the invention herein.

The artificial intraocular lens 10 (hereinafter often referred to as the "lens") generally comprises an optical zone portion 11 and a plurality of posts 12 - 15 which, in cooperation with retaining means, anchor the lens 10 in an eye. A plurality of openings 16 - 19 may be provided through the optical zone portion of the lens near the periphery thereof.

The optical zone portion 11 can be either a biconvex or planoconvex lens, as required. It is preferable that the optical zone portion be shaped similar to the natural intraocular lens insofar as is possible. The optical zone portion is preferably round in plan view and may have a diameter of 8 to 10 millimeters, which is also the overall diameter of the lens 10; however, the diameter is merely suggested and is approximately the same diameter as a human natural ocular lens, and it should be recognized that the artificial intraocular lens can and should be sized according to the eye into which it is to be implanted. The optical power of the optical zone portion 11 of the lens 10 generally is in the range of 13 to 17 diopters, with the final decision as to the exact optical power resting with the ophthalmologic surgeon who has examined the patient and is prescribing the lens. The optical zone portion 11 is preferably fabricated of a medical grade of either polymethyl methacrylate or silicone, or of another material suitable for implantation in the eye and having the requisite clarity and index of refraction for use as a lens material.

With reference to FIG. 1, the posts 12 - 15 are positioned at 90° intervals on a circle concentric with and near the periphery of the lens 10, the circle having a diameter D. Referring now to FIG. 3, the posts 12 - 15 protrude forwardly from the optical zone portion 11, and the tip of each post, for instance, post 12, is provided with an enlarged head 20 including a substantially hemispherical inner portion and a conical outer portion converging to a slightly rounded tip 21. As best seen in FIG. 5, in which the post 12 is shown in an enlarged sectional view, the post 12 comprises an inner stud 22 which is threaded at its lower end 23 into the optical zone portion 11 of the lens 10. A jacket 24 surrounds the protruding portion of stud 22 and comprises the enlarged head 20. The stud 22 is preferably fabricated of gold and the jacket 24 is preferably fabricated of either a medical grade of polymethyl methacrylate or silicone, or of another plastic material suitable for implantation in the eye. The remaining posts 13 - 15 are similar to post 12.

The openings 16 - 19 are also heated at 90° intervals on a circle concentric with and near the periphery of the lens 10, and each opening is further located 45° from each of the adjacent posts. The openings 16 - 19 are utilized in connection with means for holding and manipulating the lens 10 during implantation and/or removal thereof, and provide drain holes for aqueous produced by the ciliary body when the lens 10 is implanted in an eye.

Referring now to FIGS. 2 – 6, the retaining ring 30 is round in plan view and has an outer surface 33 which is circular in cross section. The circular outer surface is interrupted by a V-shaped slot 31 which extends around the entire retaining ring on one side thereof. The V-shaped slot 31 connects the outer surface of retaining ring 30 with an annular inner space 32 defined by the inner surface 34 of the retaining ring 30. The inner surface 34 is also circular when viewed in cross section and is concentric with the outer surface 33 of retaining ring 30. The annular space 32 and the V-shaped slot together form a slot extending entirely about the retaining ring on one side thereof, and this slot has a key hole configuration in section, being constricted at the intersection of the inner end of the V-shaped slot 31 and the annular inner space 32, as best seen in FIG. 3.

The retaining ring 30 is slightly resilient, so that the V-shaped slot 31 can be expanded to admit the heads of the posts 12 – 15. The retaining ring 30 is preferably fabricated of a medical grade of polymethyl methacrylate, silicone, or other slightly resilient material suitable for implantation in the eye. It may be either clear or tinted, as desired for cosmetic purposes.

The retaining ring 30 is adapted to be press fit onto the posts 12 – 15 and to be retained thereon by the interengaging structure of the posts and retaining ring. In particular, the mean diameter D of the V-shaped slot 31 corresponds to the diameter between opposite posts, such as posts 12 and 14, so that the points of the heads of the posts may be centrally received in the V-shaped slot 31. As the retaining ring 30 is pressed on to the posts 12 – 15, the conical outer portions of the heads of the posts enter the V-shaped slot and expand it until the retaining ring snaps over the heads of the posts. As best seen in FIGS. 4 and 5, the inner surface 34 of the retaining ring adjacent to the V-shaped slot 31 engages the hemispherical inner portions of the heads of the posts, whereby the retaining ring is secured to the posts by an interengaging fit therebetween.

Referring now to FIG. 4, there is shown an eye 40 having the artificial intraocular lens 10 and retaining ring 30 described above implanted therein. The eye 40 comprises a transparent cornea 41 which connects with the sclera 42, better known as the white of the eye. The sclera extends substantially around the entire eye except for the region of the cornea. A thin membrane 43, which is known as the conjunctiva, extends from the cornea to the underside of the eye lid, not shown. Schlemm's canal, indicated at 44, is located near the intersection of the cornea, sclera and conjunctiva. In the rear portions of the eye, not fully shown, the choroid 45 overlays the interior surface of the sclera and the retina 46 overlays the inner surface of the choroid. Near the front of the eye the choroid joins with the ciliary body, generally indicated at 47, which includes the ciliary process 50 and the ciliary muscle 51. Extending from the ciliary body is the iris 52 which defines the pupil 53. The choroid, ciliary body and iris are together known as the uveal tract, which is a vascular tract surrounding most of the eye.

The interior of the eye is substantially filled with vitreous humor 60, and the hyloid membrane 61 covers the surface of the vitreous humor. The anterior chamber of the eye is indicated at 62 and is located between the front of the iris and the cornea 41. The posterior chamber of the eye, indicated at 63, is located between the iris and the vitreous humor. The natural lens, not shown in the drawings herein, occupies the posterior chamber 63 and is held in place by zonules 64, which are shown cut as they would be during removal of the natural lens.

Referring now particularly to the iris 52, it defines the pupil 53 by virtue of a central opening therein. Sphincter and dilator muscles 54 and 55 are located in the iris adjacent to the inner periphery thereof, and control the size of the pupil. The primary expansion and contraction of the tissue of the iris takes place in the vicinity near the sphincter and dilator muscles. The stroma 56 of the iris extends between the ciliary body and the inner portion of the iris including the sphincter and dilator muscles. The stroma tissue passively folds in an accordian-like manner during dilation and contraction of the pupil. The iris tissue, including the stroma, is quite flexible and can be pulled and stretched. However, the iris has the unique property of not healing if torn or damaged. Accordingly, care should be taken in manipulating the iris.

In order to implant the artificial intraocular lens 10 and retaining ring 30 therefor, an incision is made in the cornea near Schlemm's canal, and the cornea is folded back. If implantation of the artificial intraocular lens is being undertaken because of a cataract condition, it is preferable to perform the natural lens removal and the implanation of the artificial intraocular lens in the same operation. Accordingly, the first step after opening an incision and laying back the cornea may be to perform an intracapsular or extracapsular extraction, as the condition of the patient dictates. It is anticipated that better results can be achieved in restoring vision with an artificial intraocular lens according to the invention herein if the entire natural lens is removed.

The pupil can be dilated sufficiently through the use of drugs to permit passage of the artificial intraocular lens 10 through the pupil into the posterior chamber 63 of the eye. After the lens 10 has been inserted into the posterior chamber of the eye, the posts 12 – 15 of the lens 10 may be pushed through the iris, taking care to position the iris so that the head of each post is inserted through the stroma tissue at approximately the point where it would naturally fall with the pupil in a normal condition, i.e. not dilated by drugs. The retaining ring 30 is then press fit onto the posts 12 – 15 as described above, so that the retaining ring is firmly secured upon the posts, as illustrated in FIGS. 4 – 5. The ophthalmologic surgeon may then close the eye in accordance with ordinary ophthalmologic surgical techniques.

It should be noted that the posts have a length of approximately 1½ to 2 millimeters, whereby the retaining ring 30 is sufficiently spaced from the lens 10 so that the iris is not pinched or constricted, which would disrupt circulation to the inner portions of the iris near the pupil and the constrictor and dilator muscles. The structure of the artificial intraocular lens 10 and the retaining ring 30 holds the lens firmly in the eye. In particular, the posts which extend through the iris hold the lens against lateral displacement toward the edges of the eye, and an entire ring of the stroma tissue is loosely embraced between the lens and the retaining ring to prevent the posts from pulling back through the iris. The lens is nestled against the hyloid membrane, retaining the vitreous humor from forward displacement and thereby minimizing the danger of cystoid macula endema or retinal detachment.

It should be noted that the artificial intraocular lens and retaining ring therefor, when implanted in an eye as illustrated in FIG. 4, do not compromise five key ocular anatomical areas, to wit: the endothelium or backside of the cornea; Schlemm's canal; the dilator and constrictor muscles of the pupil; the ciliary body; and the vitreous humor and hyloid membrane. By avoiding these key areas of sensitivity, complications after the implantation of the artificial intraocular lens and retaining ring are greatly reduced. The artificial intraocular lens is positioned in the posterior chamber of the eye, thereby closely duplicating the natural state and providing for restoration of good binocular vision.

Referring now to FIG. 6, the eye 40 is shown with the artificial intraocular lens 10 and retaining ring 30 implanted therein. From FIG. 6 it is apparent that the anchoring means for the lens 10 comprising the posts 12 – 15 and retaining ring 30 do not interfere with normal vision through the pupil 53.

Referring now to FIG. 7, there is shown an eye 67 wherein a sector iridectomy has been performed on the iris 68 thereof to enlarge the pupil 69 so that it extends to the periphery of the iris. The artificial intraocular lens 10 has been implanted in the eye 67 with the posts 12 – 15 arranged so that posts 13 and 14 flank the enlarged portion of pupil 69 created by the sector iridectomy. A retaining member 70 is provided for the lens 10, and the retaining member 70 comprises slightly more than 3/4 of an entire ring. The retaining member 70 is secured to the posts of lens 10 so that the enlarged pupil 69 is not blocked by the retaining member. Referring now to FIG. 8, which is a rear plan view of the retaining member 70, it can be seen that four openings 71 – 74 are provided to receive the posts 12 – 15 of the lens 10. The openings 71 – 74 are preferably slightly elongated, permitting some latitude in positioning the retaining member 70 on the posts of the lens 10. The openings 71 – 74 have a cross-sectional shape which may be similar to that shown in FIGS. 3 – 5, wherein the heads of the posts 12 – 15 may be accommodated and secured by an interengaging fit between the posts and the retaining member 70. The lens 10 is adequately held in the eye by the posts 12 – 15 and the retaining member 70, and the five key anatomical areas of the eye are protected.

Referring now to FIG. 9, the artificial intraocular lens 10 is shown with another retaining means, which comprises two retaining members 80 and 81. The retaining member 80 is curved and comprises somewhat more than ¼ of a complete ring. It is provided with elongated openings 82 and 83 positioned, respectively, near its ends for receiving and holding the posts 12 and 13 of the artificial intraocular lens 10 through an interengaging fit. The retaining member 81 is similarly provided with openings 84 and 85, which receive, respectively, posts 14 and 15. The retaining members 80 and 81 may be used with the artificial intraocular lens in implantation situations involving sector and peripheral iridectomies as well as in implantation situations in which no iridectomy is involved. A substantial portion of the stroma tissue of the iris is loosely constrained between the retaining members 80 and 81 and the lens 10, wherein the lens is adequately held in position with the eye by the posts 12 – 15 and the retaining members 80 and 81, the posts 12 – 15 are prevented from pulling back through the iris. The five key anatomical areas of the eye are fully protected when retaining members 80 and 81 are used with the lens 10.

Referring now to FIG. 10, the artificial intra-ocular lens 10 is shown together with a further embodiment of retaining means, which comprise four individual retaining buttons 90 – 93. Each of the retaining buttons 90 – 93 is substantially hemispherical and has an opening in its underside for receiving one of the heads of one of the posts 12 – 15 of the lens 10 in an interengaging fit whereby the retaining buttons 90 – 93 may be press fit on to the posts 12 – 15 and remain secured thereon. The retaining buttons 90 – 94 do not embrace as much of the stroma tissue between them and the lens 10 as do the previously described retaining members, but nevertheless the posts 12 – 15 and retaining buttons 90 – 93 do provide for sufficient anchoring of the artificial intraocular lens within the eye and effectively prevent the posts from pulling back through the iris.

Referring now to FIG. 11, there is shown an artificial intraocular lens 100 according to the invention herein. The lens 100 comprises an optical zone portion 101 having interiorly threaded openings for receiving posts 102 – 104, which protrude forwardly from the optical zone portion 101. A fourth post is not shown in FIG. 11 because the lens is shown in section, and the four posts are deployed at 90° intervals on a circle concentric with the periphery of lens 100 when viewed in plan. The post 102 comprises a stud portion 105 which is threaded along its lower end whereby the post is turned into one of the openings in the optical zone portion 101. The stud portion 105 extends forwardly from the optical zone portion 101 to a head portion of the post 102, generally indicated at 106. The head portion comprises a flange 107 which protrudes radially outwardly from the post and provides a shoulder surrounding the post. Separated from the shoulder is a rounded tip 108. The other posts 103 and 104 are similar to post 102.

A retaining disc 110 for use with the artificial intraocular lens 100 comprises a flat annular disc having four openings formed therethrough. Openings 111 and 112 can be seen in FIG. 11, and the openings are positioned about the retaining disc 110 for receiving the heads of the posts of the artificial intraocular lens 100. The retaining disc 110 is preferably fabricated of a slightly resilient material, and the round tips of the posts may be popped through the openings formed in the retaining disc wherein the retaining disc is seated against the flanges of the posts and held in that position by the round tips of the posts, as shown in FIG. 11. The posts themselves may be fabricated entirely of plastic, or may comprise an inner metal stud.

The artificial intraocular lens 100 and the retaining disc 110 may be implanted in an eye in a manner similar to that described above with respect to lens 10. The posts protruding through the iris and the retaining disc serve to anchor and position the lens 100 in the eye, while protecting the five key sensitive anatomical areas of the eye.

Referring now to FIG. 12, there is illustrated another artificial intraocular lens 115 according to the invention herein. It comprises an optical zone portion 116 having a plurality of posts, including posts 117 – 119, extending forwardly therefrom. The posts may be fabricated entirely of plastic, such as polymethyl methacrylate, as may the lens itself. The posts snugly seat in openings in the optical zone portion 116 of the lens 115 and are secured therein by sonic welding.

A retaining disc 113 is provided for use with the artificial intraocular lens 115. The retaining disc 113 comprises a flat annular disc which may be secured to the posts, after the lens has been implanted in an eye and the posts have been pushed through the iris, by positioning the retaining disc on the ends of the posts and either sonic welding the retaining disc to the posts, or by melting the retaining disc 113 and the post together through the use of a laser, as is indicated at 114. This technique is believed to be viable inasmuch as lasers are commonly used in surgery of a delicate nature, and particularly in eye surgery.

The artificial intraocular lens 115 and the retaining disc 113, being secured together by either laser or sonic welding, do not require any press fit operations to be accomplished within the eye, as do the other embodiments of artificial intraocular lenses and retaining members therefor described above. The lens 115 and retaining disc 113 have all the advantages of the previous embodiments. In particular, a substantial annular portion of the stroma is loosely embraced between the lens and the retaining disc, and the posts and the retaining disc together anchor and position the lens within the eye and prevent the posts from pulling through the iris. The sensitive areas of the eye are not disturbed by the artificial intraocular lens 115 and retaining disc 113.

This invention also relates to instruments for inserting artificial intraocular lenses as described above into the eye, and in particular, for press fitting the retaining members on to the posts of the artificial intraocular lens. The invention further relates to instruments which may be used for removing the retaining members from the posts, if necessary.

Referring now to FIG. 13, there is shown an instrument 120 according to the invention herein. The artificial intraocular lens 10 and the retaining ring 30 therefor are shown attached to the instrument 120, as will be more fully discussed below.

The instrument 120 comprises a tubular handle 121 which terminates at its lower end in a conical tip 122. As best seen in FIGS. 13, 15 and 16, a finger-like projection 123 extends forwardly from the handle 121. The finger-like projection 123 is wider at its outermost end, where a groove 124 is located. The groove 124 is shaped to matingly engage and hold a portion of the retaining ring 30.

A clamp 125 is slidably mounted to the conical tip 122 of handle 121 opposite the projection 123. The clamp 125 defines a groove 126 which is shaped to matingly engage and hold a portion of the retaining ring 30, as best seen in FIG. 15. The clamp 125 is biased by a spring 127 toward the projection 123, wherein the clamp 125 and the projection 123 cooperate to hold the retaining ring 30 therebetween.

A slidable button 130 is positioned on the side of the handle 121 for convenient thumb manipulation, and is connected by a thin wire 131 to the clamp 125. Thus, manipulation of the button 130 will pull back the clamp 125 against spring 127, thereby releasing the ring 30 held between the clamp and the projection 123.

It should be noted that the projection 123 and the clamp 125 embrace a sufficient amount of the circumference of the retaining ring 30 to adequately hold and support it, but also leave a significant portion of the ring free. Coupled with the conical tip 122 of the handle 121 and the triangular shape of the projection 123, good visibility of the retaining ring, artificial intraocular lens, and eye is provided for the ophthalmologic surgeon using the instrument 120.

The instrument 120 further comprises a barrel 135 which is slidably received inside the tubular handle 121.

A thumbwheel 136 is attached for freewheeling rotation to the upper end of handle 121, and a threaded stud 140 extends inwardly from thumbwheel 136 and is received in an interiorly threaded opening 141 in the upper end of barrel 135. Thus, rotating the thumbwheel 136 drives the barrel 135 upwardly or downwardly within and relative to the handle 121, depending upon the direction of rotation of the thumbwheel and the driven motion so imparted is both slow and controlled.

The artificial intraocular lens 10 is attached to the instrument 120 by a bridle 145. As best seen in FIG. 14, the bridle 145 comprises a generally triangular loop terminating in a tail 146. The tail 146 passes through an opening 132 in the end of the conical tip 122 of handle 121. A threaded clip 147 is secured to the end of the tail 146, and the clip 147 is threaded into an opening in the lower end of barrel 135 (see FIG. 13). Again referring to FIG. 14, the bridle 145 comprises a generally triangular loop having legs 148 - 150. Leg 148 extends from the tail 146 to drain hole 17 located near the edge of the lens 110. The bridle passes through the drain hole 17 and leg 149 of the bridle extends across the underside of the lens 110 to drain hole 19 opposite drain hole 17. The bridle also passes through drain hole 19, and the third leg 150 of the bridle extends from drain hole 19 to the tail 146. The bridle 145 is preferably fabricated of a combination of a relatively thick, semirigid wire, which may be plastic, and relatively thin and very flexible thread. The relatively thick, semirigid wire is used to form the tail 146 and leg 148 of the bridle 145, leg 148 extending from the tail 146 to the drain hole 17. The thin thread is used to form the legs 149 and 150 of the triangular loop of bridle 145 which extends across the underside of the lens 10, through the drain hole 19 and back to the tail 146. Thus, when it is desired to remove the bridle 145 from the lens 10 after the lens has been implanted in an eye, the leg 150 of the triangle may be cut and the thin thread pulled through the drain hole 19 across the back of the lens and out through drain hole 17. It would be unacceptable to pull the thick semirigid wire across the back of the lens after the lens has been implanted in an eye because of the risk of rupturing the hyloid membrane, but at least a portion of the bridle must be fabricated of such thick, semirigid wire in order that the bridle be capable of at least partially supporting the lens 10 for handling and manipulating the lens during implantation.

The bridle 145 connects the artificial intraocular lens 10 with the slidable barrel 135 of the instrument 120, and therefore rotation of the thumbwheel 136 in the desired direction causes relative movement of the lens 10 toward the retaining ring 30, being carried on the instrument 120 as described above.

Referring now to FIG. 17, the instrument 120 is shown being used in the implantation of the artificial intraocular lens 10 and its associated retaining ring 30 in eye 40. It will be appreciated that the pupil can be sufficiently dilated with the use of drugs to permit the passage of the lens 10 into the posterior chamber 63 of the eye. The stiff leg 148 of the bridle 145 provides a sufficiently strong connection between the handle of instrument 120 and the lens 10 that the instrument can be used to aid in manipulating the lens into the position shown in FIG. 17. Once the lens is so positioned and the iris 52 is placed over the posts of the lens, the thumbwheel 136 of instrument 120 is rotated to draw the bridle 145 into the instrument 120 through the opening 132 in tip 122. In order to avoid pulling the lens 10 against the iris, the surgeon moves the instrument 120 and the retaining ring 30 carried thereon toward the lens as the thumbwheel 136 is rotated.

Because the opening 132 in the tip 122 of the instrument 120 is centrally located above the retaining ring 30 held between the projection 123 and the clamp 125 (see FIG. 15) and because of the symmetrical arrangement of the posts and drain holes of the lens 10, the instrument 120 presents the lens 10 to the retaining ring 30 such that the posts 12 - 15 of the lens 10 are positioned for entry into the slot 31 on the underside of the retaining ring 30. The instrument 120 provides sufficient clearance for the surgeon using it to see if the posts are properly positioned with respect to the retaining ring. After having done so, the retaining ring is press fit on to the posts by further drawing up the bridle 145 through rotation of thumbwheel 136. As shown in FIG. 17, the iris may be pushed down over the posts simultaneously with press fitting the retaining ring onto the posts; however, the posts may be pushed through the iris prior thereto.

After the retaining ring has been seated on the posts of the lens, the thin leg 149 of bridle 145 may be cut, the retaining ring released from the instrument 120 through drawing back clamp 125, and the instrument 120 and bridle 145 removed from the eye. Thereafter, the surgeon may close the eye in accordance with normal surgical techniques.

The instrument 120 offers several important advantages in implanting artificial intraocular lenses and press fitting retaining members thereon, as described above. First, it accomplishes the centering of the retaining ring or other retaining member on the posts of the lens and press fits the retaining ring onto the posts without need for manual manipulation. Thus, such positioning and press fitting are well within the range of the average ophthalmologic surgeon. Second, the press fit of the retaining ring on to the posts of the lens is achieved gently and with no pulling, pushing, or jerking on the delicate anatomical structures of the eye. Further, the instrument affords positive control over the lens and the retaining ring during implantation thereof. Another advantage is that the implantation instrument is relatively quick, and most surgeons strongly prefer to have the eye opened for as short a time as is possible.

The instrument 120 has the still further advantage of being capable of modification for use in removing an artificial intraocular lens from an eye, if such removal is necessitated for any reason. Referring now to FIG. 18, the instrument 120 is shown with the projection 123 and the clamp 125 engaged on the retaining ring 30 which is attached to the posts of the artificial intraocular lens 10. A foot 152 is rigidly connected by a shaft 153 to the barrel 135 of the instrument 120. Therefore, rotation of the thumbwheel 136 in a direction which drives the barrel 135 downwardly within the handle 132 also drives the foot 152 against the top surface of the lens 10, and thereby accomplishes prying the retaining ring 30 from its retained position on the posts. The removal of the retaining ring is easily controlled to avoid jerking, pulling, or pushing the lens or the associated retaining ring within the eye.

Also shown in FIG. 18 is a snare 155 comprising expansible jaws 156 controlled via a control button 157, the jaws being shown clamped through drain hole 17 of the lens 10. The snare 155 is useful to retain control over the lens after the retaining ring has been removed and after the iris has been removed from the posts.

Figure 19:
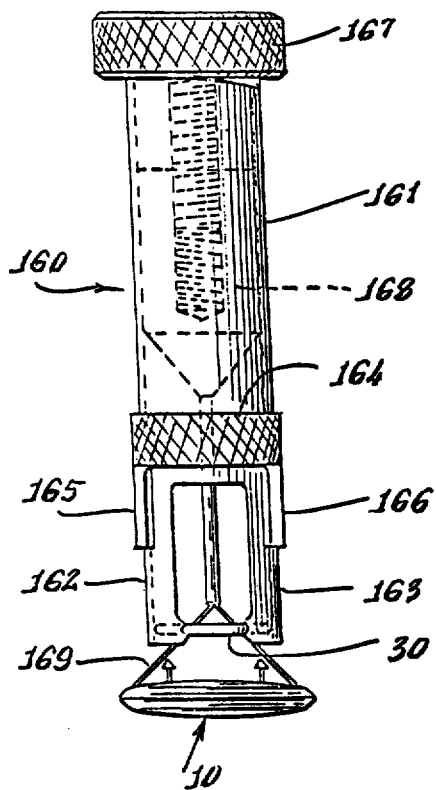
FIG. 19 is a side elevation view of an artificial intraocular lens, a retaining ring therefor, and another instrument for implanting the same within an eye, all according to the invention herein.
Figure 20:
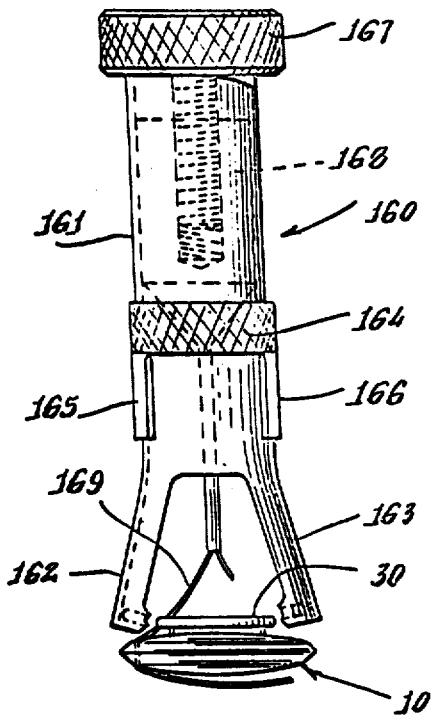
FIG. 20 is a side elevation view of the instrument of FIG. 19 expanded to release the retaining ring.

Referring now to FIGS. 19 and 20, there is shown another instrument 160 for use in implanting artificial intraocular lens as described above, and particularly in press fitting retaining members thereon. The instrument 160 generally comprises a tubular handle portion 161 terminating in two downwardly depending legs 162 and 163, which are designed to partially embrace and hold a retaining ring 30 therebetween.

In their free position, shown in FIG. 20, the legs 162 and 163 spread apart to insert or release the retaining ring 30.

A band 164 is slidably positioned around the handle 161 of the instrument 160, and the band 164 includes two tabs 165 and 166. When the band is urged downwardly along the handle 161, the tabs 165 and 166 engage the legs 162 and 163 and force them inwardly, so that they engage and hold the retaining ring 30.

The instrument 160 is provided with a thumbwheel 167 and a barrel 168 slidably mounted and driven within the handle 161 by the thumbwheel 167 in a similar manner to that described above with respect to the instrument 120. The barrel 168 is connected to the artificial intraocular lens 10 by a bridle 169, wherein rotation of the thumbwheel 167 causes relative movement of the retaining ring 30 towards the lens 10 and ultimately results in press fitting the retaining ring 30 onto the posts of the lens 10. After the retaining ring 30 has been secured to the lens 10, the band 164 is moved upwardly along the handle 161, permitting the legs 162 and 163 to spring free and release the retaining ring 30.

Good visibility for the surgeon using the instrument 160 is provided between the legs 162 and 163. Instrument 160 can also be provided with a foot and be used to remove the retaining ring from the lens, if desired.

Figure 21:
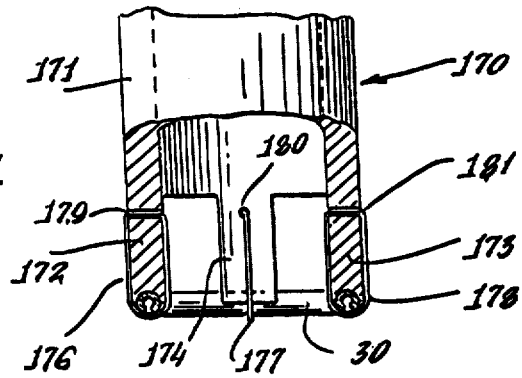
FIG. 21 is a side elevation view of an artificial intraocular lens, a retaining ring therefor, and another instrument for implanting the same within an eye, all according to the invention herein.
Figure 22:
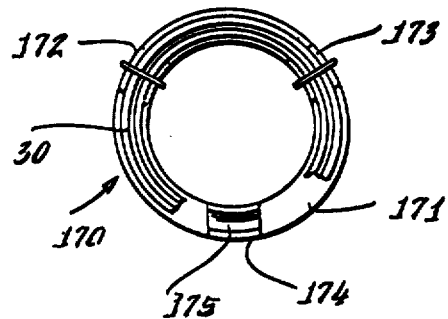
FIG. 22 is a bottom plan view of the instrument of FIG. 21.

FIGS. 21 and 22 illustrate another instrument 170 for inserting an artificial intraocular lens into an eye and for attaching a retaining member thereto, according to the invention herein. The instrument 170 comprises a handle 171 which houses a slidably mounted barrel controlled by a thumbwheel, not shown but similar to that described above. Protruding downwardly from the handle 171 are legs 172 - 174. As best seen in FIG. 22, the bottom surfaces of the legs 172 - 174 define concave grooves, such as groove 175 of leg 174, and the concave grooves together matingly receive portions of a retaining ring 30. The retaining ring 30 may be secured to the instrument 170 by thread loops 176 - 178 passed around the underside of the retaining ring and respectively through openings 179 - 181 in the upper portion of the legs 172 - 174. A bridle connects an artificial intraocular lens to the barrel of the instrument 170, similar to the manner described above and not shown in FIGS. 21 and 22, wherein the lens is driven relative to the retaining ring for press fitting the retaining ring over the posts of the lens. Thereafter, the thread loops 176 - 178 which connect the retaining rings 172 - 174 may be severed along with the bridle, and the instrument 170 removed. The instrument 170 comprises the fewest parts of the instruments described herein while retaining most of the advantages of the other instruments, and hence is a good choice for manufacutre as a disposable article.

Referring now to FIGS. 23 - 25, there is shown an artificial intraocular lens comprising an optical zone or lens portion 200 and a retaining ring 220 for anchoring the lens 200 in an eye, all according to another embodiment of the invention herein.

The lens 200 may be either a bi-convex or plano-convex lens, as required. It is preferable that it be shaped similar to the actual intraocular lens so far as is possible. The lens is preferably round in plan view and may have a diameter of 8 to 10 millimeters, as discussed with respect to lens 10 above. The lens is preferably fabricated of a medical grade of polymethyl methacrylate or of another suitable material.

The retaining ring 220 is a partial ring, as viewed in plan in FIG. 24, anticipating its use in an eye having a sector iridectomy performed thereon in a manner similar to that illustrated in FIG. 7 with respect to an earlier embodiment. It will be understood that a full ring may also be used, particularly if no iridectomy is to be performed. As best seen in FIG. 25, the retaining ring 220 has a teardrop shaped cross section and is thinner near the outer edge and is rounded on its top surface. The maximum thickness of the retaining ring 220 is preferably ½ to 1 millimeter.

Protruding from the bottom of the retaining ring 220 are three posts 221 - 223, which serve to attach the retaining ring 220 to the artificial intraocular lens 200. Posts 221 and 223 are located adjacent to the ends of the partial ring, and post 222 is centrally located therebetween. Post 221 comprises a stem portion 225 and an enlarged head portion 226, which terminates in a pointed tip 227. An opening 228 is formed transversely through the enlarged head 226 and permits the head 226 to collapse to the diameter of the stem 225 for inserting the post into openings in the lens 200, as described below. Posts 222 and 223 are similar. The retaining ring 220 and the posts 221 - 223 are preferably integral, and fabricated of polymethyl and methacrylate or other suitable material. The retaining ring may be tinted to the color of the iris of the eye into which it is being implanted for cosmetic reasons, if desired.

Referring now to FIG. 23, the lens 200 is provided with three openings 201 - 203 which receive respectively the posts 221 - 223 of the retaining ring 220. The openings 201 - 203 are arrayed on a circle concentric with and near the periphery of the lens 200, and are spaced apart along the circle so that the openings 201 - 203 align with the posts 221 - 223, as best seen in FIG. 25. The lens 200 is further provided with four openings 210 - 213 adjacent the periphery thereof, and the openings 210 - 213 are positioned at 90 degree intervals about the lens. The openings 210 - 213 extend through the lens, and provide drain passageways for aqueous produced by the ciliary body when the lens 200 is implanted in an eye, and also provide for attaching a bridle to the lens to aid in implantation and/or removal thereof, as will be described more fully below.

As best seen in FIG. 25, opening 201 includes a cylindrical central portion 206 of slightly larger diameter than the stem 225 of post 221. A beveled portion 207 surrounds opening 201 at the top surface of the lens 200. Opening 201 terminates partially through the lens 200 in a generally tear shaped portion 208, which is adapted to matingly receive the enlarged head 226 of post 221. The other openings 202 and 203 are similar in shape.

Figure 26:
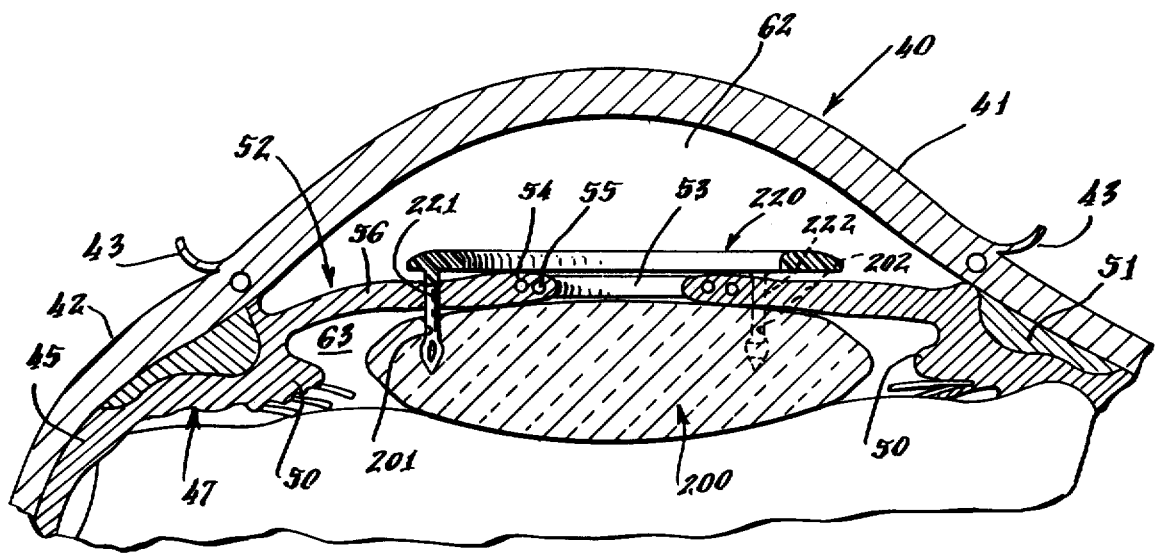
FIG. 26 is a sectional view of an eye showing the artificial intraocular lens and retaining ring of FIG. 25 implanted therein.
Figure 27:
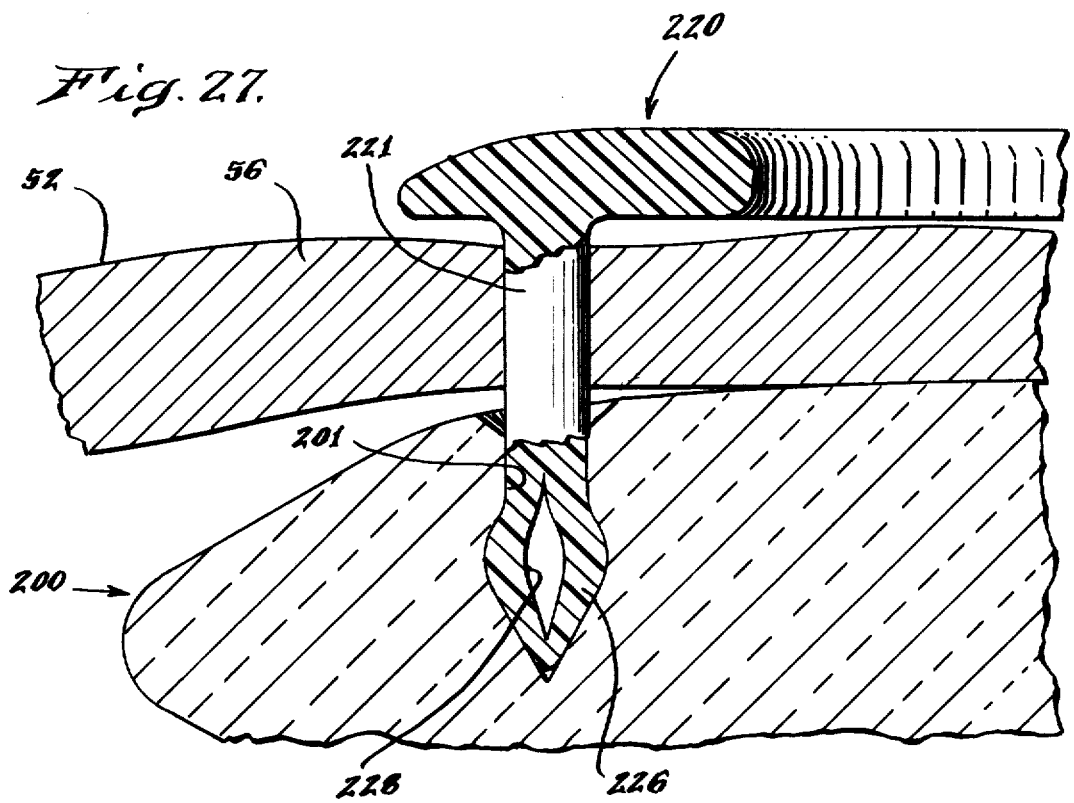
FIG. 27 is a fragmentary enlarged sectional view of a portion of the eye of FIG. 26 having the artificial intraocular lens and retaining ring implanted therein.

Referring now to FIGS. 26 and 27, there is shown an eye 40 having an artificial intraocular lens 200 and retaining ring 220 described above implanted therein. The eye 40 is the same as shown in FIG. 4 described above, and the parts of the eye have the same numbers. These parts include the cornea 41, the sclera 42, the choroid 45, the ciliary body 47, and the ciliary process 50. The eye 40 further includes the iris 52 defining a pupil 53 and having sphincter and dilator muscles 54 and 55, respectively, and stroma tissue 56. The eye 40 has an interior chamber 62 and a posterior chamber 63.

The artificial intraocular lens 200 is positioned in the posterior chamber 63 of eye 40 underlying the iris 52, and is in substantially the same position as the natural lens of the eye, removed prior to implanting the artificial intraocular lens and, accordingly, not shown in the drawings. In order to implant the artificial intraocular lens 200 and the associated retaining ring 220, an incision is made in the cornea 41 and the cornea is folded back. The pupil 53 can be dilated sufficiently through the use of drugs to permit passage of the artificial intraocular lens 200 through the pupil into the posterior chamber 63 of the eye. It should be noted that the artificial intraocular lens 200 is easily inserted into the posterior chamber as no posts protrude therefrom. After the lens 200 is in position in the posterior chamber, the retaining ring 220 is positioned above the iris with the pointed tips of posts 221 - 223 above openings 201 - 203. The posts 221 - 223 are inserted through the iris, and by virtue of their pointed tips, they capture no iris material. The bevels, such as bevel 207 of opening 201, guide the posts into the openings 201 - 203. The retaining ring 220 is moved toward the lens 200 to press the posts 221 - 223 into the openings 201 - 203. The enlarged head 226 of post 221 collapses, permitting the enlarged head to pass through the central portion 206 of opening 201. When the enlarged head 226 reaches the rounded inner portion 208 of opening 201, the enlarged head 226 expands and substantially fills the opening. This creates an interengaging "snap" fit between the opening 201 and the post 221. The remaining posts 222 and 223 and openings 202 and 203 cooperate similarly to hold the lens 200 and retaining ring 220 together. After implantation of the lens 200 and retaining ring 220, the ophthalmologic surgeon may then close the eye in accordance with ordinary surgical techniques.

It should also be noted that the configuration of posts 221 - 223 and openings 201 - 203 permit the posts to be withdrawn from the openings in order to release the retaining ring, if necessary.

The posts have a length approximately 2½ to 3 millimeters and support the retaining ring 220 approximately 1 to 1½ millimeters above the surface of the lens 200. It should be noted that the lens 200 and the retaining ring 220, when implanted in the eye 40, provide more clearance between the retaining ring 220 and the endothelium or interior surface of the cornea 41 than is provided with the lens 10 and the retaining ring 30 described above. The tear drop sectional shape of the retaining ring 220 aids in achieving greater clearance, as the retaining ring is thin at its outer edge. The clearance, of course, depends upon the particular eye in which the lens and retaining ring are implanted, but a clearance of approximately 1½ millimeters is normally expected with the lens 200 and retaining ring 220. The lens 10 and retaining ring 30 provide a clearance between the retaining ring and the endothelium of the cornea of slightly less than 1 millimeter, which is acceptable but not as advantageous as the clearance provided by this embodiment.

As in previous embodiments, the retaining ring 220 is sufficiently spaced from the lens 200 so that the iris is not pinched or constricted, and the structure of the lens 200 and retaining ring 220 holds the lens firmly in the eye. The lens 200 and retaining ring 220 also do not comprise the five key ocular anatomical areas, to wit, the endothelium of the cornea; Schlemm's canal; the dilator and constrictor muscles of the pupil; the ciliary body; and the vitreous humor and hyloid membrane. Thus, complications after implantation of the artificial intraocular lens and retaining ring are greatly reduced. The position of the lens in the posterior chamber also aids in guarding against forward displacement of the vitreous humor and consequent retinal detachment. In addition, the positioning of the lens in the posterior chamber of the eye provides for restoration of good binocular vision, and the position of the retaining ring does not interfere with the field of vision.

It will be appreciated that the number of posts depending from retaining ring 220, the configuration of the posts and openings in the lens for retaining the posts, and other details, may be altered without departing from the scope of the invention herein.

Also provided according to the invention herein is an instrument 250 particularly well adapted for implanting the artificial intraocular lens 200 and associated retaining ring 220 in an eye. The instrument 250 aids in inserting the artificial intraocular lens 200 into the posterior chamber behind the iris. It also accomplishes positioning of the retaining ring 220 and the integral posts 221 - 223 with respect to the post receiving openings 201 - 203 in the artificial intraocular lens, and press-snap fitting the posts into the lens. The instrument 250 is also well adapted for implanting the other embodiments of artificial intraocular lenses and retaining means therefor described above, and in particular, for press fitting the retaining means onto the posts extending through the iris from the lens.

The instrument 250 is illustrated in FIGS. 28 - 32. It comprises a handle 260 which is stepped at 261 and thereby divided into a thin forward portion 262 well adapted for work near the eye and a thicker rear portion 263 of a size which is comfortable in gripping and manipulating the instrument. The handle 260 defines a cylindrical opening 264 along its axis, and the forward portion 262 of the handle 260 defines an outward flared bevel or collet 265 at the forward end of opening 264. At the opposite or rear end of the handle, the opening 264 includes an enlarged portion 266 accommodating an interiorly threaded thumbwheel 268, which is mounted in a free wheeling manner to the end of handle 260 via inturned flange 267.

A shaft 270 is slidably received in the opening 264 in the handle 260. A portion of the shaft 270 extends forwardly of the handle 260 and includes two split ends 271 and 272 which are biased apart, as best seen in FIG. 32. The split ends 271 and 272 are enlarged with respect to the diameter of shaft 270 received in the opening 264, and the split ends 271 and 272 are provided with beveled surfaces 273 and 274, respectively. When the shaft 270 is retracted into the handle 260, as shown in FIGS. 28 and 29, the bevels 273 and 274 engage the collet 265 of the handle 260 and force the split ends 271 and 272 together. However, when the shaft 270 is extended forwardly with respect to the handle 260, the split ends are permitted to separate, as shown in FIG. 32.

A capture head 275 is integral with the split ends 271 and 272 of shaft 270. The capture head 275 comprises two generally semicircular discs 276 and 277 mounted to or integral with split ends 271 and 272, respectively. The discs 276 and 277 are further respectively provided with peripheral depending concave flanges 278 and 279, which are adapted to grip and hold the retaining ring 220 when the split ends 271 and 272 are biased together. When the shaft 270 is moved forward and the split ends 271 and 272 separate, the retaining ring 220 is released. Other retaining rings, described above, such as retaining ring 30 or 70, are releasably gripped by the capture head 275 in the same manner.

The instrument 250 further includes means for retracting the shaft 270 to capture and hold the retaining ring 220 and for extending the shaft 270 forward to release the retaining ring. These means include a drive collar 280 rotatably and slidably mounted about portion 263 of handle 260. The drive collar has a pin 281 mounted therein, and the pin 281 extends inwardly from the drive collar 280 through a diagonal slot 269 defined by the handle 260 and is received in a slot 283 defined crosswise in the shaft 270. A pin 284 mounted in the handle 260 extends into a longitudinal slot 285 formed in the shaft 270, and restrains the shaft 270 from rotational movement with respect to the handle 260. Thus, when the drive collar 280 is rotated to the position shown in FIG. 29, the pin 281 is positioned near the rear end of diagonal slot 269, and retracts the shaft 270 into the handle 260, thereby engaging the bevels 273 and 274 of the split ends with the collet 265 of the handle and urging the split ends together. When the drive wheel is rotated and moved forwardly along the handle 260, the pin 281 is positioned near the forward end of slot 269, and the pin 281 extends the shaft 270 forward to permit the split ends 271 and 272 of shaft 270 to separate.

The shaft 270 also defines an opening 286 along its axis, in which is carried a hollow rod 290. The hollow rod 290 extends forwardly of the capture head 275 and terminates in an offset foot 291. The foot 291 includes a bottom surface 298 against which the artificial intraocular lens 200 is held by a bridle 292. The bridle 292 may comprise a long strand of heavy suture material which extends inside the hollow rod 290 to the foot 291, where it departs from the hollow rod at opening 299. The bridle 292 is looped around the lens 200, passing through two of the drain openings 211 and 213, which are diametrically opposed. The foot 291 further includes two notches 293 and 294, which are diametrically opposed, and which serve to guide the bridle from the foot and also serve to hold the lens from rotating with respect to the foot. Alternatively, the foot 291 may comprise a suction fitting to hold the lens via suction applied through rod 290.

It should be noted that the foot 291 is also adapted to hold the other embodiments of lenses described above, such as lens 10.

The opposite end of the hollow rod 290 is provided with a threaded sleeve 295, which may be press fit over the rod 290, and the threaded sleeve 295 mates with the interiorly threaded thumbwheel 268. Thus, rotation of the thumbwheel 268 drives the rod 290 together with foot 291 and lens 200 attached thereto away from or toward the capture head 275. The threaded sleeve 295 extends through the thumbwheel 268, and a threaded cap 296 is attached over the end of the threaded sleeve, engaging the bridle 292. More particularly, the bridle 292 may be pulled tight and secured in its tight condition holding the lens against the foot by means of cap 296.

The rod 290 includes a slot 287 into which pin 284 extends, thereby preventing rotation of rod 290 with respect to shaft 270 and handle 260. Thus, the lens 200 and the retaining ring 220 can be accurately positioned such that the posts 221 - 223 will enter the openings 201 - 203 as thumbwheel 268 is rotated to move the retaining ring and lens together.

The instrument 250 is used in implanting the artificial intraocular lens 200 and the retaining ring 220 in the following manner. First, the retaining ring 220 is positioned in the capture head 275 and the drive collar 280 is rotated to retract shaft 270 into the handle 260, thereby urging the split ends 271 and 272 closed to firmly grip the retaining ring 220. The artificial intraocular lens 200 is held against the bottom surface 298 of foot 291 of rod 290 by passing the bridle 292 through the drain holes 211 and 213, aligning the bridle in the notches 293 and 294, the tightening the bridle and securing it in its tightened position by cap 296. Thumbwheel 268 is rotated to extend the rod 290 and the lens 200 forward with respect to the handle. With the lens so extended, the instrument 250 is used to insert the lens through the pupil to its position underlying the iris. Thereafter, thumbwheel 268 is rotated to cause relative movement of the retaining ring 220 toward the lens 200, the surgeon taking care to move the handle forwardly to bring the retaining rings 220 into position over the lens and not to pull the lens back through the pupil. Inasmuch as the retaining ring 220 is firmly held by the capture head and the lens 200 is firmly held against the foot 291, and the retaining ring and the lens are positioned such that the posts 211 – 223 of the retaining ring are presented to the openings in the lens, further rotational of thumbwheel 268 causes the posts 221 – 223 to puncture the iris and press-snap into the openings 201 – 203 in lens 200. The bevels surrounding the openings 201 – 203 aid in guiding the posts into the openings. Some flexure of the posts occurs during this procedure, but it is insufficient to cause damage to the posts.

Once the retaining ring 220 is attached to the lens 200 via the posts 221 – 223, drive collar 280 is rotated to release the retaining ring from the capture head 275. Threaded cap 296 is then rotated to relase the bridle 292 so that the instrument can be withdrawn. The bridle is then severed and removed from around the lens 200.

The instrument 250 is used in the same manner in implanting other embodiments of artificial intraocular lenses, such as lens 10 and retaining ring 30, except that the instrument then operates to press the retaining ring onto the posts.

The instrument 250 may also be used to remove retaining rings from previously implanted lenses by gripping the retaining ring in the capture head and thereafter driving the foot 291 forward by means of thumbwheel 268.

Although the instruments described above are capable of accurately and repetitively assembling the lens portion and retaining means of the artificial intraocular lenses also described above, it would nevertheless be desirable for the surgeon implanting the artifical intraocular lenses to be sure that the proper engagement of the posts has been achieved. This is particularly important with embodiments of the artificial intraocular lenses such as lens 200 and its associated retaining ring 220 wherein the engagement of the posts is in openings in the lens portion positioned behind the iris and not visible. However, confirmation of the engagement is also desirable in the other embodiments of the lenses described above, wherein extra instrumentation such as microscopes and extra time during the surgical technique is required to visually check the engagement of the posts with the retaining means.

In order to obviate this problem, portions of the artificial intraocular lenses according to the invention herein can be made of electrically conductive materials, and contacts of an electrical circuit can be temporarily engaged with the artificial intraocular lenses such that an electrical circuit is completed through the artificial intraocular lenses when the posts are operatively engaged. The electrical circuit provides an extra-ocular confirmation signal which informs the surgeon immediately when operative engagement of the posts has been achieved.

Referring now to FIGS. 33 – 35, there is shown an artificial intraocular lens comprising an optical zone or lens portion 300 and a retaining ring 320 for anchoring the lens 300 in an eye, all according to another embodiment of the invention herein.

The lens 300 may be either a bi-convex or plano-convex lens, are required. It is preferable that it be shaped similar to the actual intraocular lens so far as is possible. The lens is preferably round in plan view and may have a diameter of 7 to 8 millimeters.

The retaining ring 320 is a partial ring, as viewed in plan in FIG. 34, anticipating its use in an eye having a sector iridectomy performed thereon in a manner similar to that illustrated in FIG. 7 with respect to an earlier embodiment. It will be understood that a full ring may also be used. As best seen in FIG. 35, the retaining ring 320 has a teardrop shaped cross section and is thinner near the outer edge and is rounded on its top surface. The outside diameter of the retaining ring 320 may be slightly less than the diameter of the lens portion 300.

Protruding from the bottom of the retaining ring 320 are three posts 321 – 323, which serve to attach the retaining ring 320 to the lens 300. Posts 321 and 323 are located adjacent to the ends of the partial ring, and post 322 is centrally located therebetween. Post 321 comprises a stem portion 325 which terminates in a pointed tip 327. Post 321 is press fit into and extends through the retaining ring 320, and the end 326 of post 321 protrudes slightly above the top surface of retaining ring 320, as viewed in FIG. 35. A semicircular slot opening 328 is formed transversely into the stem 325 for securing the post in openings in the lens 300, as described below. Posts 322 and 323 are similar. The retaining ring 320 preferably fabricated of polymethyl and methacrylate or other suitable electrically insulating material, and the posts 321 – 323 are fabricated of a conductive material, such as gold or platinum, the latter being somewhat preferable for its greater strength. The posts are coated with a thin layer of insulating material 324, except at slot 328 and end 326. The insulating material may also be polymethyl methacrylate. The retaining ring may be tinted to the color of the iris of the eye into which it is being implanted for cosmetic reasons, if desired.

Referring now to FIG. 33, the lens 300 is provided with three openings 301 – 303 which receive respectively the posts 321 – 323 of the retaining ring 320. The openings 301 – 303 are arrayed on a circle concentric with and near the periphery of the lens 300, and are spaced apart along the circle so that the openings 301 – 303 align with the posts 321 – 323, as best seen in FIG. 35. The lens 300 is further provided with four openings 310 – 313 adjacent the periphery thereof, and the openings 310 – 313 are positioned at 90° intervals about the lens. The openings 310 – 313 extend through the lens, and provide drain passageways for aqueous produced by the ciliary body when the lens 300 is implanted in an eye, and also provide for attaching a bridle to the lens to aid in implantation and/or removal thereof, as described above with respect to lens 200.

The lens portion 300 defines a peripheral groove 305 thereabout which extends inwardly from the edge of the lens portion 300. The groove 305 intersects the openings 301 – 303 and extends approximately half way through them. A split ring 306 is received in groove 305, with the ends 307 and 308 of the split ring 306 being separated from each other and positioned between openings 301 and 303. The split ring 306 is fabricated of a conductive material suitable for implantation in an eye, such as gold or platinum. Platinum is preferred over gold as it has more stiffness and results in a split ring having sufficient "memory" characteristics to be expanded for assembly in groove 305 and to thereafter seat snugly in groove 305 and function as a split ring spring. The split ring 306 extends approximately half way into the openings 301 – 303, as best seen in FIGS. 36 and 37.

Referring now to FIGS. 36 and 37, there is shown an eye 40 having an artificial intraocular lens 300 and retaining ring 320 described above implanted therein. The eye 40 is the same as shown in FIG. 4 described above, and the parts of the eye have the same numbers. These parts include the cornea 41, the sclera 42, the choroid 45, the ciliary body 47, and the ciliary process 50. The eye 40 further includes the iris 52 defining a pupil 53 and having sphincter and dilator muscles 54 and 55, respectively, and stroma tissue 56. The eye 40 has an anterior chamber 62 and a posterior chamber 63.

The artificial intraocular lens 300 is positioned in the posterior chamber 63 of eye 40 underlying the iris 52, and is in substantially the same position as the natural lens of the eye, removed prior to implanting the artificial intraocular lens and, accordingly, not shown in the drawings. In order to implant the artificial intraocular lens 300 and the associated retaining ring 320, an incision is made in the cornea 41 and the cornea is folded back. The pupil 52 can be dilated with drugs, but its intrinsic elasticity will permit passage of the artificial intraocular lens 300 through the pupil into the posterior chamber 63 of the eye. It should be noted that the artificial intraocular lens 300 is easily inserted into the posterior chamber as no posts protrude therefrom. After the lens 300 is in position in the posterior chamber, the retaining ring 320 is positioned above the iris with the pointed tips of posts 321 – 323 above openings 301 – 303. The posts 321 – 323 are inserted through the iris, and by virtue of their pointed tips, they capture no iris material. Bevels, such as bevel 304 of opening 301, guide the posts into the openings 301 – 303. The retaining ring 320 is moved toward the lens 300 to press the posts 321– 323 into the openings 301 – 303. The pointed tip 327 of post 321 spreads the split ring 306 and permits the post to slide by. When the slot 328 reaches the split ring 306, the split ring contracts and snaps into slot 328. This creates an interengaging "snap" fit between the lens portion 300 and the post 321, best seen in FIG. 37. The remaining posts 322 and 323, openings 302 and 303, and split ring 306 cooperate similarly to hold the lens 300 and retaining ring 320 together.

It should also be noted that the configuration of posts 321 – 323, openings 301 – 303, and split ring 306 permit the posts to be withdrawn from the openings in order to release the retaining ring, if necessary.

The posts have a length approximately 2½ to 3 millimeters and support the retaining ring 320 approximately 1 to 1½ millimeters above the surface of the lens 300. The tear drop sectional shape of the retaining ring 320 aids in achieving greater clearance, as the retaining ring is thin at its outer edge, as described above with respect to lens 200 and retaining ring 220.

As in previous embodiments, the retaining ring 320 is sufficiently spaced from the lens 300 so that the iris is not pinched or constricted, and the structure of the lens 300 and retaining ring 320 holds the lens firmly in the eye. The lens 300 and retaining ring 320 also do not compromise the five key ocular anatomical areas, to wit, the endothelium of the cornea; Schlemm's canal; the dilator and constrictor muscles of the pupil; the ciliary body; and the vitreous humor and hyloid membrane. Thus, complications after implantation of the artificial intraocular lens and retaining ring are greatly reduced. The position of the lens in the posterior chamber also aids in guarding against forward displacement of the vitreous humor and consequent retinal detachment. In addition, the positioning of the lens in the posterior chamber of the eye provides for restoration of good binocular vision, and the position of the retaining ring does not interfere with the field of vision.

The advantage of the lens 300 and retaining ring 320 described above over the other embodiment disclosed herein is that they are adapted to form part of an electrical circuit, the electrical circuit in turn providing an extra-ocular confirmation signal to indicate that the posts and lens are properly operatively engaged. In particular, split ring 306 of lens 300 is conductive, and the posts are also conductive, e.g. post 321 is conductive but is insulated by insulation 324 except at the slot 328 and the end 326, the other posts being similar. Thus, when the slot 328 of the post 321 is engaged with the split ring 306, electrically conductive contact is achieved therebetween, but if the slot 328 of post 321 is not so engaged, there is no electrically conductive contact.

The split ring 306 of lens 300 and the posts 321 – 323 of retaining ring 320 are shown connected into an electrical circuit 340 in FIG. 38 and into an alternate electrical circuit 350 in FIG. 39. FIG. 40 illustrates how the capture head 275 of instrument 250 is modified to mount the electrical circuit and indicator, and to connect the circuit.

Referring first to FIG. 38, the electrical circuit 340 comprises a DC power source 341, two resistors 342 and 343, two light emitting diodes 344 and 345, and connecting wires. Light emitting diodes 344 and 345 may be model Nos. 5082-4100 of Hewlett Packard and resistors 342 and 343 may be 510 ohm, ¼ watt (5%) carbon composition resistors. The DC power source may be a three-volt battery, and its positive terminal is connected across the resistor 342 and light emitting diode 344 to the end of post 323. The end of post 322 is connected to the negative terminal of the battery 341. If posts 322 and 323 are operatively engaged with split ring 306, electrical contact between them is established and the electrical circuit is completed through the posts, 322, 323 and split ring 306 which causes light emitting diode 344 to light. The positive terminal of battery 341 is also connected across the resistor 343 and light emitting diode 345 to the end 326 of post 321. If both posts 321 and 322 are operatively engaged with the split ring 306, electrical contact is established between them and the electrical circuit is completed through the posts 321, 322 and split ring 306 to light light emitting diode 345. When both light emitting diodes 344 and 345 are lighted, the desired extra-ocular confirmation signal is thereby obtained, and the ophthalmologic surgeon knows that the posts 321 – 323 of the retaining ring 320 are operatively engaged with the split ring 306 in the lens 300.

FIG. 39 illustrates an alternative circuit 350 which comprises two batteries 351 and 352, two resistors 353 and 354, and one light emitting diode 355. In circuit 350 the batteries 351 and 352 may be of 1.5 volts each, the resistors 353 and 354 may be 1,000 ohm, ⅛ watt (5%) carbon composition resistors, and the light emitting diode 355 may be model Nos. 5082-4100 manufactured by Hewlett Packard. If electrical contact is established between posts 321, 322 and split ring 306, the battery 351 is connected to provide approximately one-half the current necessary to light the light emitting diode 355. If the post 323 is also operatively engaged with split ring 306, the battery 352 is connected to provide the remaining one-half the current necessary to light the light emitting diode 355. Thus, if the three posts 321 – 323 are all operatively engaged with the split ring 306, the light emitting diode 355 lights to provide an extra-ocular confirmation signal of this desired condition.

The values of the resistors in both circuits 340 and 350 presume low contact resistance between the posts 321 – 323 and the split ring 306, as well as low losses throughout the remainder of the circuits. However, the resistors values can be adjusted easily to compensate for such losses upon their quantitative determination. It will also be understood that other circuits, which may be relatively simple, can be substituted for those shown, and that those circuits shown are illustrative only. It is also understood that other signal means, such as signal means producing audible or even tactile sensed signals, could be used, as well as visual signals other than light emitting diodes, such as a simple indicator light.

FIG. 40 illustrates how the capture head 275 of instrument 250 can be modified to mount the electrical circuit, such as circuit 340, and to connect the conductive split ring 306 of the lens 300 and posts 321 - 323 of retaining ring 320 into the circuit. As described above, the capture head 275 embraces and holds the retaining ring 220, and it operates in a similar manner with respect to retaining ring 320. However, two contact terminals 360 and 361 are mounted to the capture head 275, surrounded respectively by insulating pads 362 and 363, and the contact terminals 360 and 361 are positioned to contact the ends of posts 321 and 323, respectively. The end of post 322 contacts the instrument itself, which serves as a ground in the circuit. A circuit housing 366 is attached to the instrument 250 and contains the battery, light emitting diodes 344 and 345, and the resistors 342 and 343. Two wires 367 and 368 run from the contact terminals 360 and 361 to the elements of electrical circuit 340 in housing 366. Thus, the circuit is self-contained on the instrument and the sign provided by the light emitting diodes is readily visible to the ophthalmological surgeon as he uses the instrument 250 to implant the lens 300 and its associated retaining ring 320.

In carrying out the implant technique, it is preferable to first engage the posts 321 - 323 of retaining ring 320 with the lens 300. This assures that the posts 321 - 323 and the openings 301 - 303 in the lens are correctly aligned, and provides visual signals from light emitting diodes 344 and 345 which confirm that the circuit is working and the proper contacts are made. Then the lens 300 and the retaining ring 320 are separated, and are implanted as described above with respect to lens 200 and retaining ring 220. When the posts 321 - 323 of retaining ring 320 are operatively engaged with the split ring 306 of lens 300, then positioned behind the iris, the light emitting diodes 344 and 345 light. The ophthalmological surgeon may then remove the lens 300 from the instrument 250 by releasing and cutting the bridle, and may then close the eye in accordance with the usual surgical technique.

It will be appreciated that the key to providing the extra-ocular confirmation signal is the conductive paths established through conductive surfaces which are in operative engagement when the posts and lens are correctly assembled. Many modifications can be made from the design described above while still achieveing its purposes.

As one example, another artificial intraocular lens 370 including a retaining ring 375 is illustrated in FIG. 41. The lens 370 includes openings, such as opening 371 for receiving posts depending from the retaining ring 375, such as post 376. A conductor 372 is embedded in the lens 370 and is exposed at the bottom of the opening, where it is contacted by a conductive pin 377 comprising a part of post 376. Contact is established between the conductor 372 and the conductive pin 377 of post 376 when the post is operatively engaged in the opening 371. The posts of the retaining ring 375 and the conductive element 372 of lens 370 may be connected in an electrical circuit the same as or similar to those described above to provide an extra-ocular confirmation signal that the correct operative engagement has been achieved.

As noted above, it is also desirable to provide an extra-ocular confirmation signal in connection with those embodiments of artificial intraocular lenses wherein the posts protrude from the lens portion and engage the retaining ring.

FIGS. 42 - 44 illustrate an artificial intraocular lens 380 and associated retaining ring 390, which are similar in structure and operation to the lens 10 and associated retaining ring 70 described above. However the lens 380 and retaining ring 390 are modified to provide an extra-ocular confirmation signal when the posts and ring are operatively engaged.

In particular, the lens 380 includes four posts 381 – 384 which protrude forwardly from the front surface of the lens. The posts are conductive, and posts 381 and 382 are connected by a conductive member 385 embedded in the lens, and the posts 383 and 384 are connected on a conductive element 386 also embedded in the lens. Drain holes 388 are provided through the lens 380.

The retaining ring 390 has four conductive terminals 391 – 394 extending therethrough, each terminal aligned with the tip of one of the posts 381 – 384. As best seen in FIG. 44, the top of post 381 contacts the terminal 391 when the retaining ring is operatively engaged on the post. Contact between the other posts and terminals is similarly achieved. The instrument for holding and attaching the retaining ring 390, such as instrument 120, may be modified in a manner similar to that described above with respect to instrument 250 to provide further contact terminals for connecting the contact terminals 391 – 394 of the retaining rings to an electrical circuit for providing the desired extra-ocular confirmation signal, wherein the path of the electrical circuit passes through the contact terminals of the retaining ring, the posts, and the conductive elements embedded in the lens.

An example of such an electrical circuit 400 is illustrated in FIG. 45. The electrical circuit 400 comprises a battery 401, a resistor 402, and a light emitting diode 403, which are connected across the terminals 391 and 392 of the retaining ring 390. When the retaining ring is operatively engaged on the posts 381 and 382, the circuit is completed through the posts 381, 382 and the conductive element 385 embedded in the lens 380, whereupon the light emitting diode 403 lights. The remaining portion of the electical circuit 400 is similar, and comprises a battery 405, a resistor 406, and a light emitting diode 407, which are connected across the contact terminals 394 and 393 of the retaining ring 390. The light emitting diode 407 lights when the circuit is completed through posts 383, 384, and the conductive element 386 embedded in the lens.

It will be apparent to those skilled in the art that various modifications of the artificial intraocular lenses and instruments described herein can be made without departing from the spirit and scope of the invention. For instance, the number of posts and the precise positioning of the posts may be altered, and similarly, the number of drain holes and their positions can be altered. Other materials may be suitable for fabricating artificial intraocular lenses according to the invention herein, and the materials disclosed herein merely provide acceptable examples. Other circuits and configurations for completing the circuits by operative engagement of the lens and retaining means may also be used without departing from the concept of providing an extra-ocular confirmation signal to inform the surgeon that the proper engagement has been achieved. The sizes of the artificial intraocular lenses may be changed, particularly when the lenses are to be used in animals. The lenses may be somewhat thinner than the natural lens, whether human or animal, and such thinner lenses are nevertheless considered as being shaped "similar" to the natural lens. The instruments may also be modified, as for instance to accept various configurations of retaining members. Similarly, the thumbwheel drive means could be replaced by other drive means achieving relative movement between an artificial intraocular lens and a retaining member therefor. Also, other means for holding and manipulating the lenses may be employed. For instance, the artificial intraocular lenses can be held and manipulated by conventional forceps, or by provision of a flexible tipped instrument having an opening therethrough to which suction is applied, wherein the lens is held to the instrument by vacuum and released from the instrument by releasing the suction. With respect to the technique of implanting the artificial intraocular lenses described herein, various ophthalmologic surgeons may develop different techniques dictated by their own skills and preferences.

The artificial intraocular lenses, retaining members, and instruments for implantation thereof described above are believed to efficiently achieve the objects of the invention. The usefulness and advantages of the artificial intraocular lenses, retaining members, and the instruments aiding implantation thereof will be readily apparent to those skilled in the art.

Accordingly, the above description of the preferred embodiments is to be construed as illustrative only rather than as limiting, and the scope of the invention is defined in the following claims.

We claim:

1. An artificial intraocular lens for implantation into the posterior chamber of an eye, the artificial intraocular lens comprising an optical zone portion fabricated of transparent material and shaped similar to a natural lens, and retaining means having a plurality of posts attached thereto and extending rearwardly therefrom, the ends of said posts adapted to be operatively engaged with said optical zone portion, wherein said optical zone portion may be implanted in the posterior chamber of an eye and said retaining means may be positioned in the anterior chamber of the eye with the posts protruding rearwardly from said retaining means through the iris and into the posterior chamber of the eye where said posts are operatively engaged with said optical zone portion, said retaining means and posts thereby together holding and positioning the artificial intraocular lens within the eye, and wherein the posts of said retaining means and the optical zone portion have conductive surfaces which contact upon operative engagement and which are adpated for connection into an electrical circuit providing a signal upon such contact, said signal comprising extra-ocular confirmation of the operative engagement.

2. An artificial intraocular lens as defined in claim 1 wherein all of the plurality of posts must be operatively engaged with the optical zone portion in order for an extra-ocular confirmation signal to be produced.

3. An artificial intraocular lens as defined in claim 1 wherein the posts are conductive and are received in openings in the optical zone portion, and said optical zone portion comprises at least one conductive member exposed in at least two of the openings and contacting the conductive posts received therein to provide a conducting path therebetween, wherein the conducting path comprises a necessary portion of the electrical circuit providing an extra-ocular confirmation signal.

4. An artificial intraocular lens as defined in claim 3 wherein said retaining means comprises a single retaining member having a plurality of spaced-apart posts protruding rearwardly therefrom.

5. An artificial intraocular lens as defined in claim 4 wherein said retaining member is substantially three-fourths of a full ring and has three spaced-apart posts extending rearwardly therefrom, and said conductive member contacts each of the three posts when the posts are operatively engaged with said optical zone portion.

6. An artificial intraocular lens as defined in claim 5 wherein said conductive posts extend through said retaining ring and the ends of said conductive posts are exposed adjacent the top of said retaining ring, whereby the ends of the conductive posts are conveniently positioned for connection into an electrical circuit providing a signal upon operative engagement of said posts with said optical zone portion, said signal being extra-ocular confirmation of the operative engagement.

7. An artificial intraocular lens as defined in claim 3 wherein the optical zone portion defines a peripheral groove intersecting the post-receiving openings, and wherein said conductive member is positioned in the peripheral groove and thereby exposed in the post-receiving openings.

8. An artificial intraocular lens as defined in claim 4 wherein said conductive member comprises a split ring spring extending into said post-receiving openings, and said posts each define a slot partially therethrough which receives said split ring spring to operatively engage said posts in the optical zone portion.

9. An artificial intraocular lens as defined in claim 3 wherein said post-receiving openings extend partially through the optical zone portion, and at least one conductive member is embedded in the optical zone portion and exposed at the bottoms of said post-receiving openings, whereby the conductive posts contact the conductive member when they are operatively engaged in the openings.

10. An artificial intraocular lens as defined in claim 3 and further comprising electrical circuit means including a power source and signal producing means, and means for contacting the conductive posts and connecting them to the electrical circuit, wherein said signal producing means is operated by said power source when a conductive path is established through the conductive posts and conductive member of the optical zone portion.

11. An artificial intraocular lens as defined in claim 10 wherein said signal means produces a visible signal.

12. An artificial intraocular lens as defined in claim 11 wherein said signal means comprises at least one light emitting diode.

13. An artificial intraocular lens as defined in claim 10 wherein said signal means produces an audible signal.

14. An artificial intraocular lens as defined in claim 10 wherein said signal means produces a tactile signal.

15. An artificial intraocular lens as defined in claim 10 wherein said means for contacting the conductive posts comprises an instrument for implanting said artificial intraocular lens, said instrument comprising a capture head for releaseably holding the retaining means and conductive means contacting the conductive posts extending from said retaining means.

16. An artificial intraocular lens for implantation in the posterior chamber of an eye, the artificial intraocular lens comprising an optical zone portion fabricated of transparent material and shaped similar to a natural lens, a plurality of posts attached to the optical zone portion near the periphery thereof and extending forwardly therefrom, and retaining means adapted to be operatively engaged with the ends of said posts, wherein said artificial intraocular lens may be imprinted in the posterior chamber of an eye with the posts protruding forwardly from the optical zone portion through the iris and into the anterior chamber of the eye, and wherein said retaining means may be operatively engaged with the ends of the posts in the anterior chamber of the eye, wherein said posts and retaining means together hold and position the lens within the eye and prevent the posts from pulling through the iris thereof, and wherein the posts of said retaining means and the optical zone portion have conductive surfaces which contact upon operative engagement and which are adapted for connection into an electrical circuit providing a signal upon such contact, said signal comprising extra-ocular confirmation of the operative engagement.

17. An artificial intraocular lens as defined in claim 16 wherein all of the plurality of posts must be operatively engaged with the retaining means in order for an extraocular confirmation signal to be produced.

18. An artificial intraocular lens as defined in claim 16 wherein the posts are conductive and said optical zone portion comprises at least one conductive member connecting at least two of the posts to provide a conducting path therebetween, wherein the conducting path comprises a necessary portion of the electrical circuit providing an extra-ocular confirmation signal.

* * * * *